US011771436B2

(12) United States Patent
Cibulski et al.

(10) Patent No.: US 11,771,436 B2
(45) Date of Patent: Oct. 3, 2023

(54) ANEURYSM TREATMENT DEVICE AND METHOD

(71) Applicant: Perflow Medical Ltd., Natania (IL)

(72) Inventors: Gilad Cibulski, Zur-Moshe (IL); Avraham Rapaport, Tel-Aviv (IL); Danny Farin, Adanim (IL); Itamar Bonneau, Tel-Aviv (IL)

(73) Assignee: Perflow Medical Ltd., Natania (IL)

( * ) Notice: Subject to any disclaimer, the term of this patent is extended or adjusted under 35 U.S.C. 154(b) by 379 days.

(21) Appl. No.: 16/992,179

(22) Filed: Aug. 13, 2020

(65) Prior Publication Data

US 2020/0367902 A1  Nov. 26, 2020

Related U.S. Application Data

(62) Division of application No. 15/500,142, filed as application No. PCT/IL2015/050803 on Aug. 5, 2015, now Pat. No. 10,792,043.
(Continued)

(51) Int. Cl.
*A61F 2/90* (2013.01)
*A61B 17/12* (2006.01)
(Continued)

(52) U.S. Cl.
CPC .... *A61B 17/12118* (2013.01); *A61B 17/1214* (2013.01); *A61B 17/12172* (2013.01);
(Continued)

(58) Field of Classification Search
CPC .............. A61B 17/12118; A61B 17/12; A61B 17/1214; A61B 17/12172; A61F 2/90;
(Continued)

(56) References Cited

U.S. PATENT DOCUMENTS 5,951,599 A   9/1999  McCrory
6,093,199 A   7/2000  Brown et al.
(Continued)

FOREIGN PATENT DOCUMENTS

CN   1556689    12/2004
CN   101426454   5/2009
(Continued)

OTHER PUBLICATIONS

Notice of Reason(s) for Rejection dated Jan. 26, 2021 From the Japan Patent Office Re. Application No. 2017-506765 and Its Translation Into English.(.
(Continued)

*Primary Examiner* — Vi X Nguyen

(57) ABSTRACT

An intravascular device for treating a cerebral aneurysm which has an externally controllable expandable member, the expandable member has a plurality of wires that define walls of the expandable member; where in a relaxed state of the expandable member the walls have at least a first wall portion in which openings defined between the wires are small enough to prevent coils positioned within the aneurysm from exiting the aneurysm, the first wall portion has an axial length at least as long as a neck of the aneurysm; and at least a second wall portion in which openings defined between the wires are large enough to allow blood flow through; the second wall portion axially aligned relative to the first wall portion.

11 Claims, 23 Drawing Sheets

Related U.S. Application Data

(60) Provisional application No. 62/107,607, filed on Jan. 26, 2015, provisional application No. 62/034,263, filed on Aug. 7, 2014.

(51) Int. Cl.
    *A61F 2/966*     (2013.01)
    *A61F 2/82*     (2013.01)
    *A61F 2/95*     (2013.01)

(52) U.S. Cl.
    CPC ............... *A61F 2/90* (2013.01); *A61F 2/966* (2013.01); *A61B 17/1204* (2013.01); *A61B 2017/1205* (2013.01); *A61F 2/95* (2013.01); *A61F 2002/823* (2013.01); *A61F 2002/9505* (2013.01); *A61F 2002/9665* (2013.01); *A61F 2230/0097* (2013.01); *A61F 2250/0015* (2013.01); *A61F 2250/0039* (2013.01)

(58) Field of Classification Search
    CPC ...... A61F 2/95; A61F 2/966; A61F 2002/823; A61F 2002/9505; A61F 2002/9665; A61F 2002/9522
See application file for complete search history.

(56) References Cited

U.S. PATENT DOCUMENTS

| | | | |
|---|---|---|---|
| 6,454,795 | B1 | 9/2002 | Chuter |
| 8,562,667 | B2 | 10/2013 | Cox |
| 2003/0100945 | A1 | 5/2003 | Yodfat et al. |
| 2003/0109917 | A1 | 6/2003 | Rudin et al. |
| 2003/0139802 | A1 | 7/2003 | Wulfman et al. |
| 2003/0220683 | A1 | 11/2003 | Minasian et al. |
| 2004/0093063 | A1 | 5/2004 | Wright et al. |
| 2005/0267568 | A1 | 12/2005 | Berez et al. |
| 2006/0259131 | A1 | 11/2006 | Molaei et al. |
| 2008/0045995 | A1 | 2/2008 | Guterman et al. |
| 2008/0161936 | A1* | 7/2008 | Feller ............... A61B 17/12172 623/23.76 |
| 2009/0264988 | A1 | 10/2009 | Mafi et al. |
| 2010/0114017 | A1 | 5/2010 | Lenker et al. |
| 2010/0137973 | A1 | 6/2010 | Sutermeister et al. |
| 2010/0280587 | A1 | 11/2010 | Ortiz et al. |
| 2011/0213403 | A1 | 9/2011 | Aboytes |
| 2011/0264132 | A1 | 10/2011 | Strauss et al. |
| 2012/0290067 | A1* | 11/2012 | Cam ......................... A61F 2/86 29/527.1 |
| 2013/0116774 | A1* | 5/2013 | Strauss ............ A61B 17/12172 623/1.35 |
| 2014/0018843 | A1 | 1/2014 | Berez et al. |
| 2014/0074149 | A1 | 3/2014 | Garcia et al. |
| 2014/0128901 | A1 | 5/2014 | Kang et al. |
| 2014/0343663 | A1* | 11/2014 | Sudin ............... A61B 17/12031 623/1.15 |
| 2017/0265869 | A1 | 9/2017 | Cibulski et al. |

FOREIGN PATENT DOCUMENTS

| | | |
|---|---|---|
| CN | 101589972 | 12/2009 |
| CN | 102639181 | 8/2012 |
| CN | 102743207 | 10/2012 |
| CN | 104068912 | 10/2014 |
| EP | 2165684 | 3/2010 |
| JP | 2004-130068 | 4/2004 |
| JP | 2008-502378 | 1/2008 |
| JP | 2011-516183 | 5/2011 |
| WO | WO 97/25000 | 7/1997 |
| WO | WO 03/007823 | 1/2003 |
| WO | WO 2005/115118 | 12/2005 |
| WO | WO 2009/124288 | 10/2009 |
| WO | WO 2014/028913 | 2/2014 |
| WO | WO 2014/087245 | 6/2014 |
| WO | WO 2016/020922 | 2/2016 |

OTHER PUBLICATIONS

Notification of Office Action and Search Report dated Dec. 29, 2020 From the State Intellectual Property Office of the People's Republic of China Re. Application No. 201910109980.1 and Its English Summary of Office Action Into English. (13 Pages).

Translation Dated Jan. 19, 2021 of Notification of Office Action dated Dec. 29, 2020 From the State Intellectual Property Office of the People's Republic of China Re. Application No. 201910109980.1. (8 Pages).

Applicant-Initiated Interview Summary dated Feb. 18, 2020 From the US Patent and Trademark Office Re. U.S. Appl. No. 15/500,142. (3 pages).

Applicant-Initiated Interview Summary dated May 29, 2019 From the US Patent and Trademark Office Re. U.S. Appl. No. 15/500,142. (3 Pages).

Communication Pursuant to Article 94(3) EPC dated Dec. 2, 2019 From the European Patent Office Re. Application No. 15829490.0. (5 Pages).

Communication Pursuant to Article 94(3) EPC dated Mar. 6, 2018 From the European Patent Office Re. Application No. 15829490.0. (4 Pages).

Communication Pursuant to Article 94(3) EPC dated Apr. 15, 2019 From the European Patent Office Re. Application No. 15829490.0. (6 Pages).

International Preliminary Report on Patentability dated Feb. 16, 2017 From the International Bureau of WIPO Re. Application No. PCT/IL2015/050803. (9 Pages).

International Search Report and the Written Opinion dated Feb. 8, 2016 From the International Searching Authority Re. Application No. PCT/IL2015/050803.

Invitation to Pay Additional Fees dated Dec. 16, 2015 From the International Searching Authority Re. Application No. PCT/IL2015/050803.

Notice of Reasons for Rejection dated May 14, 2019 From the Japan Patent Office Re. Application No. 2017-506765 and Its Translation Into English. (21 Pages).

Notice of Reasons for Rejection dated Apr. 21, 2020 From the Japan Patent Office Re. Application No. 2017-506765 and Its Translation Into English. (21 Pages).

Notification of Office Action and Search Report dated Nov. 27, 2017 From the State Intellectual Property Office of the People's Republic of China Re. Application No. 201580043568.4 and Its Translation of Office Action Into English. (14 Pages).

Notification of Office Action dated Jul. 11, 2018 From the State Intellectual Property Office of the People's Republic of China Re. Application No. 201580043568.4 and Its Translation of Office Action Into English. (17 Pages).

Official Action dated Jun. 6, 2019 From the US Patent and Trademark Office Re. U.S. Appl. No. 15/500,142. (16 Pages).

Official Action dated Nov. 19, 2019 From the US Patent and Trademark Office Re. U.S. Appl. No. 15/500,142. (20 pages).

Official Action dated Jan. 29, 2019 From the US Patent and Trademark Office Re. U.S. Appl. No. 15/500,142. (25 Pages).

Restriction Official Action dated Oct. 19, 2018 From the US Patent and Trademark Office Re. U.S. Appl. No. 15/500,142. (10 Pages).

Supplementary European Search Report and the European Search Opinion dated Feb. 12, 2018 From the European Patent Office Re. Application No. 15829490.0. (10 Pages).

Communication Pursuant to Article 94(3) EPC dated Aug. 19, 2022 From the European Patent Office Re. Application No. 15829490.0. (6 Pages).

Notice of Reasons for Rejection dated May 17, 2022 From the Japan Patent Office Re. Application No. 2021-088555 and Its Translation Into English. (22 Pages).

Notification of Office Action and Search Report dated Jun. 2, 2021 From the State Intellectual Property Office of the People's Republic of China Re. Application No. 201910109980.1 and Its Translation of Office Action Into English. (15 Pages).

Notification of Office Action and Search Report dated Aug. 23, 2021 From the State Intellectual Property Office of the People's Republic of China Re. Application No. 201910109980.1. (8 Pages).

(56) References Cited

OTHER PUBLICATIONS

Translation Dated Sep. 1, 2021 of Notification of Office Action dated Aug. 22, 2021 From the State Intellectual Property Office of the People's Republic of China Re. Application No. 201910109980.1. (6 Pages).

* cited by examiner

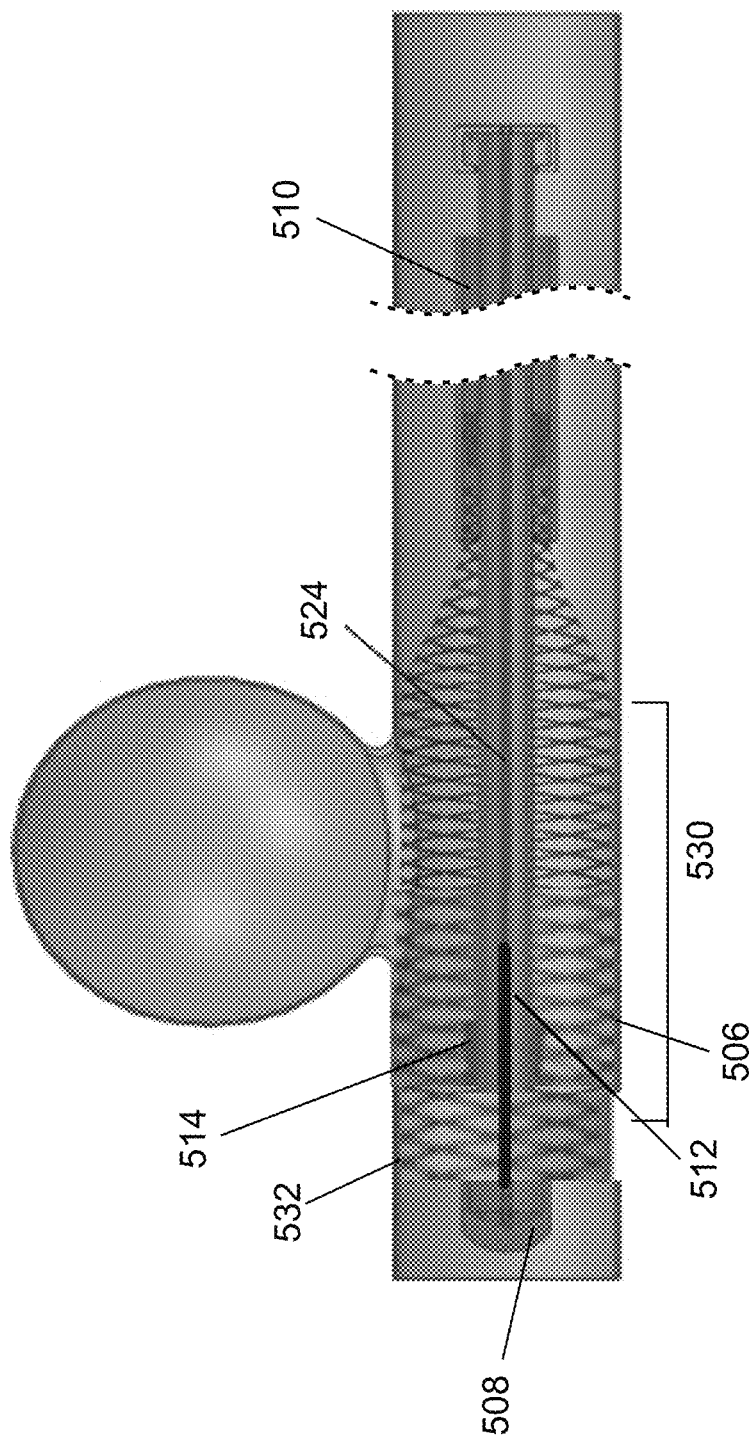

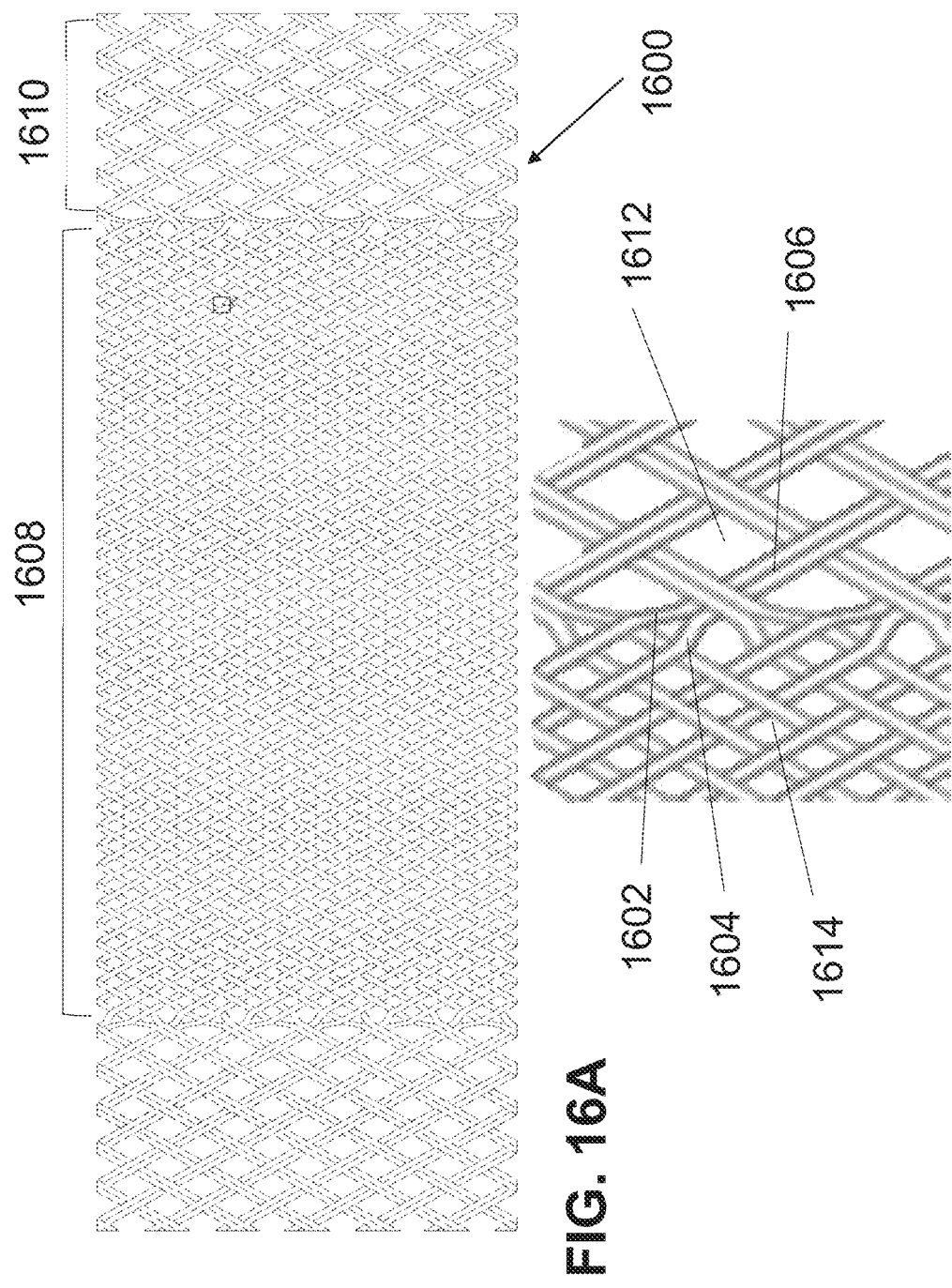

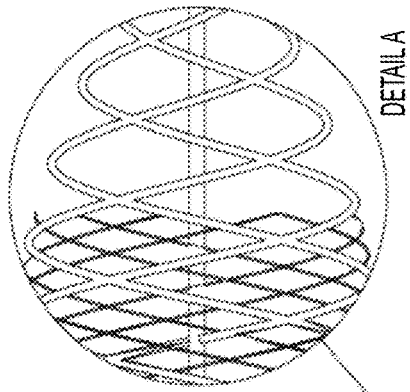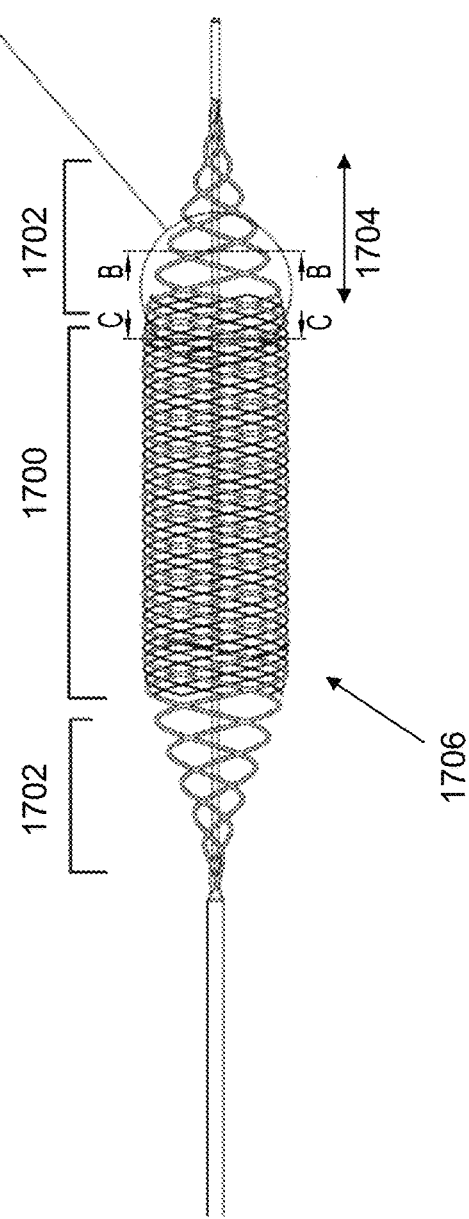

SECTION B-B

SECTION A-A

ANEURYSM TREATMENT DEVICE AND METHOD

RELATED APPLICATIONS

This application is a division of U.S. patent application Ser. No. 15/500,142 filed on Jan. 30, 2017, which is a National Phase of PCT Patent Application No. PCT/IL2015/050803 having International Filing Date of Aug. 5, 2015, which claims the benefit of priority under 35 USC § 119(e) of U.S. Provisional Patent Application No. 62/034,263 filed Aug. 7, 2014 and of U.S. Provisional Patent Application No. 62/107,607 filed Jan. 26, 2015. The contents of the above applications are all incorporated by reference as if fully set forth herein in their entirety.

FIELD AND BACKGROUND OF THE INVENTION

The present invention, in some embodiments thereof, relates to devices and methods for treating an aneurysm, and, more particularly, but not exclusively, to an adjustable intravascular device for obstructing flow to and/or from a cerebral aneurysm at a level sufficient to enable a thrombotic reaction to take place.

US publication number US20030109917 A1 to Rudin et al. discloses "a stent including a variable porosity, tubular structure having pores defined by structural surfaces. The tubular structure has a low porosity region on a path around the tubular structure, where the low porosity region is less porous than other regions located on the path and fully or partially obstructs passage of fluid. The low porosity region is larger than the structural surfaces between adjacent pores. Also disclosed is a method of altering blood flow within and near an opening of a defective blood vessel involving deploying the above stent of the present invention in a defective blood vessel so that the low porosity region is aligned to and in contact with an opening in the defective blood vessel, thereby altering blood flow within and near the opening of the defective blood vessel."

SUMMARY OF THE INVENTION

According to an aspect of some embodiments of the invention, there is provided an intravascular device for treating a cerebral aneurysm, the device comprising an externally controllable expandable member, the expandable member comprising a plurality of wires that define walls of the expandable member; wherein in a relaxed state of the expandable member the walls comprise: at least a first wall portion in which openings defined between the wires are small enough to prevent coils positioned within the aneurysm from exiting the aneurysm, the first wall portion comprising an axial length at least as long as a neck of the aneurysm; and at least a second wall portion in which openings defined between the wires are large enough to allow blood flow through; the second wall portion axially aligned relative to the first wall portion.

According to some embodiments of the invention, the openings of the first wall portion are small enough to reduce radial blood flow to and/or from the aneurysm.

According to some embodiments of the invention, openings of the second wall portion are large enough to allow radial blood flow through.

According to some embodiments of the invention, the expandable member substantially does not interfere with non-radial blood flow in the vessel.

According to some embodiments of the invention, the expandable member comprises a tubular shape, wherein the first wall portion comprising the small openings defines a central segment of the tubular shape, and the second wall portion comprising large openings defines a proximal end segment and a distal end segment of the tubular shape.

According to some embodiments of the invention, an axial length of the central segment is at least as long as an axial length of the aneurysm neck. According to some embodiments of the invention, wires forming the first wall portion are paired to each other to form the second wall portion. According to some embodiments of the invention, a ratio between a cross sectional area of an opening at the first wall portion and a cross sectional area of an opening at the second wall portion is between 1:1.5 and 1:3.8. According to some embodiments of the invention, the first wall portion comprises 42 wires, and the second wall portion comprises 21 double stranded wires.

According to some embodiments of the invention, some of the wires that form the first wall portion are cut-off or are looped around other wires, so that only some of the wires that form the first wall portion extend to form the second wall portion.

According to some embodiments of the invention, a cross sectional area of an opening at the first wall portion is smaller than a maximal cross sectional area of an intra-aneurismal coil in its non-linear, curled-up form.

According to some embodiments of the invention, a push/pull cable extends through a lumen of the expandable member, the cable operatively coupled to a first element, the first element movable relative to a second element, at least the second element coupled to the expandable member; the cable axially pullable and pushable from outside the body to modify a diameter of the expandable member by moving the first element relative to the second element.

According to some embodiments of the invention, the second element is an outer tube, the outer tube coupled to a proximal end of the expandable member by a detachable interface providing for removal of the outer tube. According to some embodiments of the invention, at least some of the wires comprise a flat cross section profile.

According to some embodiments of the invention, the device further comprises a securing tube, the securing tube surrounding the expandable member, the securing tube axially displaceable with respect to a lumen of the expandable member, the securing tube comprising one or more wedges rigidly attached to an internal wall of the securing tube, the wedges located between the outer tube and the expandable member to limit movement of the expandable member.

According to some embodiments of the invention, the first element is a cup coupled to a distal end of the push/pull cable; the cup axially movable relative to the outer tube to axially compress the expandable member and increase its diameter when pulled in a proximal direction by the cable or extend the expandable member and decrease its diameter when advanced in a distal direction by the cable. According to some embodiments of the invention, the device comprises one or more radiopaque wires or wire segments.

According to some embodiments of the invention, the radiopaque wires or wire segments are positioned for orienting the expandable member relative to a long axis of the member, the radiopaque wires positioned at one or both of a periphery and center of the first wall portion, thereby facilitating aligning the first wall portion with the aneurysm neck.

According to an aspect of some embodiments of the invention, there is provided an intravascular device for treating a cerebral aneurysm, the device comprising an expandable member, the expandable member comprising an inner wire cage comprised within an outer wire cage.

According to some embodiments of the invention, openings of the inner cage do not or only partially overlap with openings of the outer cage. According to some embodiments of the invention, an overlapping area between an opening of the outer cage and an opening of the inner cage is modifiable. According to some embodiments of the invention, the overlapping area is modifiable by axially sliding the inner cage relative to the outer cage or vice versa.

According to some embodiments of the invention, the overlapping area is modifiable by rotating the inner cage relative to the outer cage or vice versa. According to some embodiments of the invention, the inner cage expands to a relaxed diameter larger than the outer cage to fittingly engage the outer cage. According to some embodiments of the invention, the inner cage is coupled to the outer cage by one or more attachment points, the attachment points located at non-junction segments of wires forming the cages.

According to some embodiments of the invention, the attachment point comprises a welded connection between one or more wires of the inner cage and one or more wires of the outer cage.

According to some embodiments of the invention, expansion or contraction of the outer cage expands or contracts the inner cage respectively. According to some embodiments of the invention, dimensions of the inner cage and dimensions of the outer cage are controlled simultaneously. According to some embodiments of the invention, dimensions of the inner cage and dimensions of the outer cage are controlled separately.

According to an aspect of some embodiments of the invention, there is provided an intravascular device for treating a cerebral aneurysm, the device comprising: an expandable member, the expandable member comprising a tubular body shaped and sized for fitting within a cerebral blood vessel; the expandable member comprising plastically deformable members interweaved with elastically deformable members.

According to some embodiments of the invention, the plastically deformable members are annealed wires. According to some embodiments of the invention, a yield strength of a material from which the elastically deformable members is comprised of is at least 3 times a yield strength of a material from which the plastically deformable members are comprised of.

According to some embodiments of the invention, a number of the plastically deformable members is sufficient to maintain the expandable member in a selected configuration. According to some embodiments of the invention, a push/pull cable extends through a lumen of the expandable member and is coupled to a distal end of the expandable member, the plastically deformable members deformable in response to axial force applied to the cable.

According to an aspect of some embodiments of the invention, there is provided a method of treating a cerebral aneurysm, comprising positioning an expandable member in a cerebral blood vessel at a location of an aneurysm, the expandable member comprising a plurality of wires arranged to define at least one dense wall portion having openings that are smaller than one or more other wall portions of the expandable member; expanding the expandable member to engage the blood vessel walls; and allowing the dense wall portion to interfere with inner content of the aneurysm exiting the aneurysm.

According to some embodiments of the invention, the inner content comprises blood contained within the aneurysm. According to some embodiments of the invention, the inner content comprises intra-aneurismal coils that were previously introduced into the aneurysm. According to some embodiments of the invention, the method comprises reducing radial flow into and/or out the aneurysm enough to allow a thrombus to form. According to some embodiments of the invention, the method further comprises adjusting a diameter of the expandable member from outside the patient's body; and retracting a delivery system used for the positioning to temporarily or permanently deploy the expandable member in the vessel. According to some embodiments of the invention, the adjusting is performed based on a clotting rate of blood at a location of the aneurysm. According to some embodiments of the invention, the method further comprises delivering one or more coils into the aneurysm to induce the clotting.

According to some embodiments of the invention, the coils are introduced into the aneurysm through a lumen of the expandable member.

According to some embodiments of the invention, the coils are introduced into the aneurysm via a microcatheter at least partially axially aligned with the expandable member, and wherein the method further comprises expanding a diameter of the expandable member to capture the microcatheter between the expandable member and a wall of the blood vessel to prevent movement of the microcatheter during coil deployment.

According to some embodiments of the invention, the method further comprises removing the microcatheter after coils were deployed and further expanding a diameter of the expandable member. According to some embodiments of the invention, the aneurysm location is at a neck of a saccular aneurysm. According to some embodiments of the invention, the aneurysm location is along a substantial length of a fusiform aneurysm.

According to some embodiments of the invention, the expanding comprises allowing at least a wall portion of the expandable member to slightly protrude into a neck of the aneurysm. According to some embodiments of the invention, the retracting comprises releasing a distal end of the expandable member from a cup element in which it is crimped, the distal end self expanding to match a diameter of a more proximal portion of the expandable member.

According to some embodiments of the invention, the expandable member includes a first cage and a second cage. According to some embodiments of the invention, the positioning comprises positioning the first cage and the second cage. According to some embodiments of the invention, the expanding comprises expanding the first cage and said second cage sequentially.

According to an aspect of some embodiments of the invention, there is provided a method of treating a cerebral aneurysm, comprising: positioning a first expandable member in a cerebral blood vessel at a location of an aneurysm; and expanding the first expandable member to engage the blood vessel walls. According to some embodiments of the invention, the method comprises positioning a second expandable member within the first expandable member and expanding the second expandable member.

According to an aspect of some embodiments of the invention, there is provided a kit for treating a cerebral aneurysm, comprising: a delivery system comprising at least one outer tube shaped and sized for introducing an expandable member into a cerebral blood vessel; a plurality of expandable members of various relaxed diameters, wherein each of the expandable member comprises a wire mesh defining at least one wall portion in which openings between the wires are small enough to reduce radial blood flow to and/or from the aneurysm.

According to an aspect of some embodiments of the invention, there is provided an intravascular device for treating a cerebral aneurysm, the device comprising an expandable member controllable from outside the body, the expandable member comprising a plurality of wires that define walls of the expandable member; wherein in a relaxed state of the expandable member the walls comprise: at least a first wall portion in which openings defined between the wires are small enough to reduce radial blood flow to and/or from the aneurysm, the first wall portion comprising an axial length at least as long as a neck of the aneurysm; and at least a second wall portion in which openings defined between the wires are large enough to allow blood flow through; the second wall portion axially positioned relative to the first wall portion.

According to an aspect of some embodiments of the invention, there is provided an intravascular device comprising: an expandable member comprising a plurality of wires that define walls of the expandable member; the expandable member comprising, in a relaxed state of the member, at least a first axial segment and a second axial segment, the first axial segment comprising a cross sectional diameter larger than a cross sectional diameter of the second axial segment; and a push/pull cable extending longitudinally within a lumen of the expandable member, the push/pull cable coupled to a distal end of the expandable member; the cable configured to be manipulated from outside the body to modify at least one of a diameter of the first axial segment and a diameter of the second axial segment.

According to an aspect of some embodiments of the invention, there is provided an intravascular device for treating a cerebral aneurysm, the device comprising an expandable member controllable from outside the body, the expandable member comprising a plurality of wires that define walls of the expandable member; wherein in a relaxed state of the expandable member the walls are arranged to define at least one dense wall portion having openings that are smaller than one or more other wall portions of the expandable member.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A-5D illustrate deployment of an expandable member in a blood vessel exhibiting an aneurysm and optional retraction of the delivery system, according to some embodiments of the invention;

FIGS. 16A-16B are exemplary wire structures of an expandable member comprising pairing of wires, according to some embodiments of the invention;

FIGS. 17A-17D show an exemplary wire arrangement of an expandable member comprising a varying number of wires, according to some embodiments of the invention;

DESCRIPTION OF SPECIFIC EMBODIMENTS OF THE INVENTION

Figure 1A:
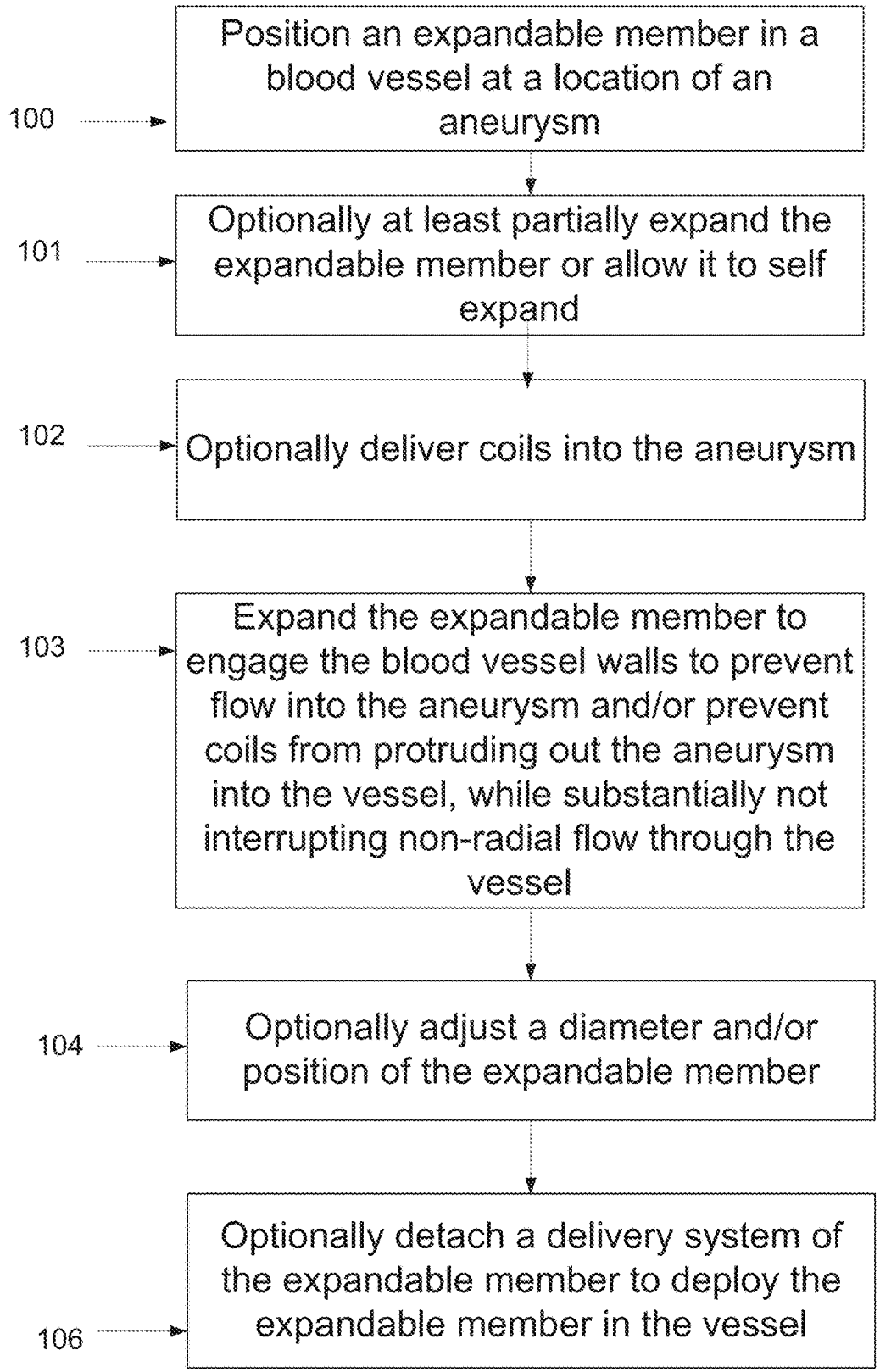
FIGS. 1A-1B are flowcharts of methods of deploying an expandable member in a blood vessel exhibiting an aneurysm, according to some embodiments of the invention.

The present invention, in some embodiments thereof, relates to devices and methods for treating an aneurysm and, more particularly, but not exclusively, to an adjustable intravascular device for obstructing flow to and/or from a cerebral aneurysm at a level sufficient to enable a thrombotic reaction to take place.

Some embodiments of the invention relate to a device comprising an expandable member configured to fittingly engage walls of a blood vessel at a location of an aneurysm, such as a saccular or a fusiform aneurysm, to obstruct sufficient flow to and/or from the aneurysm to allow a thrombus to form and/or to prevent from one or more coils which have optionally been introduced into the aneurysm from protruding out of the aneurysm and into the vessel.

In some embodiments, the expandable member comprises a tubular or balloon-like (e.g. elliptical) structure, formed of a plurality of wires. Optionally, the wires are weaved into a braided mesh.

In some embodiments, the device comprises a mechanism for selectively modifying one or more diameters of the expandable member. In some embodiments, the mechanism comprises a push/pull cable which is operatively coupled to the expandable member, and is movable relative to an outer tube from which the expandable member extends. In some embodiments, the cable extends in a proximal direction to be manipulated by a user from outside the body.

In some embodiments, a diameter of the expandable member is adjusted a plurality of times, for example to obtain a close fit of at least a portion of the walls of the expandable member to walls of the blood vessel exhibiting the aneurysm. Additionally or alternatively, the expandable member is expanded and/or contracted to modify a positioning of the member in the vessel, for example to axially advance or retract the member, such as by a rippling movement obtained upon repetitive expansion and contraction.

In some embodiments, the extent of radial expansion is determined according to a coagulation rate of blood. Optionally, the extent of expansion is selected according to an indication of flow stasis which is effective to eventually seal the aneurysm. In such a case, a physician may expand the expandable member until an initial indication of sufficient flow stasis is obtained (for example using imaging).

An aspect of some embodiments relates to a geometry of an expandable member, in which the member in its relaxed, non-manipulated state comprises at least one section in which openings defined between the wires are small enough to reduce radial flow to and/or from an aneurysm and/or small enough to prevent coils that were introduced into the aneurysm from exiting the aneurysm, and at least one section in which openings between the wires are large enough to allow flow through them, such as allow axial flow through the blood vessel and/or allow radial flow at non-aneurysm locations. In some embodiments, the expandable member comprises a central segment of a higher density which is intended to be aligned, at least in part, with an aneurysm neck, and proximal and distal segments of a lower density which substantially do not interfere with non-radial flow through the vessel. Optionally, the one or more segments of lower density are positioned axially relative to the dense segment.

In some embodiments, an opening of the expandable member at the dense segment comprises a cross sectional area which is smaller than a maximal cross sectional area of a curled-up coil within the aneurysm, to prevent the coil from exiting the aneurysm. Additionally or alternatively, a cross sectional area of the opening of the expandable member at the dense segment is smaller than a cross sectional area of the coil wire itself (i.e. in a planar, non-curled form). In some embodiments, a relatively dense wall portion of the expandable member which comprises small openings relative to one or more other portions of the expandable member comprises an axial length which is at least as long as a neck of the aneurysm. In an example, the expandable member comprises a dense central segment which extends over at least 30%, at least 50%, at least 70%, at least 80% or intermediate, larger or smaller percentages of a total length of the expandable member. Optionally, the expandable member comprises one or more portions of lower density, for example at the proximal and/or distal ends of the member, extending over a total of, for example, 20%, 30%, 50% or intermediate, larger or smaller percentages of a total length of the expandable member.

Various configurations of an expandable member structured to least interfere with non-radial flow through the vessel while sufficiently obstructing an aneurysm to promote healing of the aneurysm are described herein, in accordance with some embodiments of the invention.

An aspect of some embodiment relates to an expandable member in which an effective number of wires varies at different portions of the member, for example reduced at proximal and/or distal portions of the member to form a portion of reduced density relative to a central portion of the member. In some embodiments, the reduction is obtained by pairing wires together, for example pairing two wires into a double stranded wire. In some embodiments, the reduction is obtained by terminating (e.g. by cutting off) a plurality of wires that are comprised within the more dense portion of the member, for example a central portion of the member, so that only a selected smaller number of wires extend to form the proximal and/or distal portions of the member. In some embodiments, effectively reducing the number of wires increases a size of the openings defined between the intercrossing wires, for example to a ratio of 1:1.9, 1:1.7, 1:1.5 or intermediate, larger or smaller ratios of an opening at a more dense portion of the member relative to an opening at a less dense portion of the member. In another example, if the wires are paired by a gradual wire pairing (e.g. two wires paired into one double stranded wire, and then two double stranded wires are paired into one 4-stranded wire), a ratio between an opening at a more dense portion of the member and an opening at a less dense portion of the member may range between, for example, 1:3, 1:3.5, 1:3.8 or intermediate, larger or smaller ratios. In some embodiments, paired wires and/or reduced number of wires of the member compensate for an effective reduction in the size of the openings at the distal and/or proximal ends of the member, which may occur due to crimping of the end portion (e.g. into a cup element for example as further described herein).

An aspect of some embodiments relates to an expandable member comprising two or more wire cages, fitted one within the other. In some embodiments, an inner wire cage extends axially within an outer wire cage. Optionally, the inner cage extends within a central portion of the outer cage, and does not extend to proximal and/or distal portions of the outer cage, forming a relatively high density central portion. Optionally, the cages are layered over each other in a manner in which the openings of the cages only partially overlap or do not overlap with each other, increasing the density. In some embodiments, the cages are coupled to each other by an over-size fit, in which the inner cage expands to a relaxed diameter larger than a diameter of the outer cage, and is restrained by the outer cage. In some embodiments, the cages are coupled to each other via a plurality of attachment points. Optionally, the attachment points are located at non-junction wire segments, for example located along a wire segment between two neighboring junctions in which two or more wires cross each other.

In some embodiments, the inner cage can be simultaneously controlled, for example by expanding and/or contracting the outer cage. Additionally or alternatively, the inner and outer cages can be separately controlled. Optionally, the openings of the cages are re-arranged relative to each other (e.g. by increasing or decreasing an overlapping area between the openings), to modify the summed opening density of the expandable member.

In some embodiments, an inner cage and an outer cage are separate components, optionally delivered separately (e.g. sequentially). In some embodiments, after delivery of a first cage, a second cage is delivered by the same or a second microcatheter.

An aspect of some embodiments relates to an expandable member comprising a combination of elastic members and plastic members. In some embodiments, plastic members in the form of annealed wires are interwoven with elastic or super-elastic wires. In some embodiments, the expandable member is deformable into a selected configuration, and can be maintained in that configuration with the aid of the plastic members. In some embodiments, the expandable member is shaped (e.g. by expanding, contracting, lengthening and/or shortening the member) to anatomically fit a vessel portion in which it is located. For example, at least a portion of the expandable member may slightly protrude into the basis of the aneurysm neck, contributing to sealing of the neck. Optionally, the expandable member is configured to remain in the selected configuration until force over a certain threshold is applied, for example a pulling or pushing force applied to the cable to expand or contract the member.

An aspect of some embodiments of the invention relates to a device comprising a detachable delivery system. In some embodiments, the expandable member is introduced into the vessel and adjusted to a desired configuration, using one or more tubes and a shape-modifying mechanism (e.g. a diameter and/or length and/or axial position modifying mechanism, for example comprising a push/pull cable as described herein).

In some embodiments, for example when permanent or semi-permanent deployment of the expandable member in the vessel is required, the delivery system is detached from the expandable member and retracted out of the body, while the expandable member remains in the vessel. Optionally, detachment is operated by movement of the push/pull cable, for example movement of the cable relative to an outer tube through which the expandable member was introduced.

In some embodiments, the deployed expandable member remains held in the set position inside the vessel due to radial force applied by the walls of the expandable member onto the walls of the vessel. Optionally, elastic properties of the member are utilized to provide for detaching the delivery system, for example by the distal and/or proximal ends of the member naturally expanding to comply with the central portion of the expandable member that is already engaged with the vessel walls, for example upon release of the proximal end of the member from the outer tube and/or release of a distal end of the member from a cup in which it was crimped.

In some embodiments, an aneurysm is coiled while an expandable member is positioned in the vessel. In some embodiments, one or more coils are introduced into the aneurysm to induce thrombosis. In some embodiments, the coils are delivered into the aneurysm adjacent the expandable member, for example by maintaining the expandable member in a non expanded or partially expanded configuration during delivery of the coils (e.g. through a microcatheter inserted adjacent the member), and then expanding the member to obstruct the aneurysm neck to prevent the coils from exiting the neck. In some embodiments, the expandable member is selectively expanded to a diameter which will force a distal end of the coil-delivering microcatheter into the aneurysm and/or assist in maintaining the microcatheter in place, such as "trap" the microcatheter in between the expandable member and the vessel wall. Optionally, the expandable member is further expanded once the coil-delivering microcatheter is removed, optionally until the expandable member is fully engaged with the vessel walls. Additionally or alternatively, coils are delivered through a lumen of the expandable member. Optionally, the one or more coils are passed through the mesh openings of the member. In an example, the coil-delivering microcatheter is passed through the one or more mesh openings of the member and into the aneurysm neck, and the coils are advanced from a distal opening of the microcatheter into the aneurysm. Additionally or alternatively, the expandable member is expanded to engage the vessel walls, and when the coil delivering microcatheter is introduced it is passed between the outer walls of the expandable member and the vessel wall. Optionally, the coil delivering microcatheter is squeezed between the expandable member and the vessel wall. Optionally, the expandable member assists in maintaining the microcatheter in place so that it does not move during coil delivery.

It is noted that the expandable member may comprise various shapes, such as a balloon-like (elliptic) shape, in which a proximal and/or distal ends of the wire mesh are crimped or are otherwise clumped together; a cylindrical shape; an hourglass shape and/or any other profiles. In some embodiments, the expandable member is symmetrical with respect to the longitudinal axis and/or with respect to the transverse axis of the member. Alternatively, the member is asymmetrical, for example having a first wall portion which is located (at an initial relaxed configuration and/or at an expanded or contracted configuration) at a radius larger than a second wall portion of the member, for example to engage the aneurysm neck on the side of the vessel wall in which the first member wall portion is positioned and least interrupt flow on the opposite side of the vessel (which does not exhibit the aneurysm) in which the second member wall portion is located.

It is noted that while some embodiments of the invention are described with respect to a cerebral blood vessel exhibiting an aneurysm, the devices and/or methods described herein may be suitable for treating vasculature other than the cerebral vessels, such as aortic vasculature and/or abdominal vasculature and/or peripheral vasculature.

The term "proximal", as referred to herein, may include a direction corresponding with the user end (e.g. physician interface), for example being a direction in which the device is introduced to the vessel. The term "distal" as referred to herein may include a direction corresponding with a more distant vessel location, farthest away from user end of the device.

The term "relaxed state" as referred to herein may include a non-manipulated state of the expandable member, for example including a manufactured configuration, a non-collapsed and/or non-expanded configuration, a self-expanding configuration, a pre-loaded configuration (e.g. before coupling the member to one or more components of the delivery system), an outside the body configuration, and/or other non-manipulated forms of the member.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
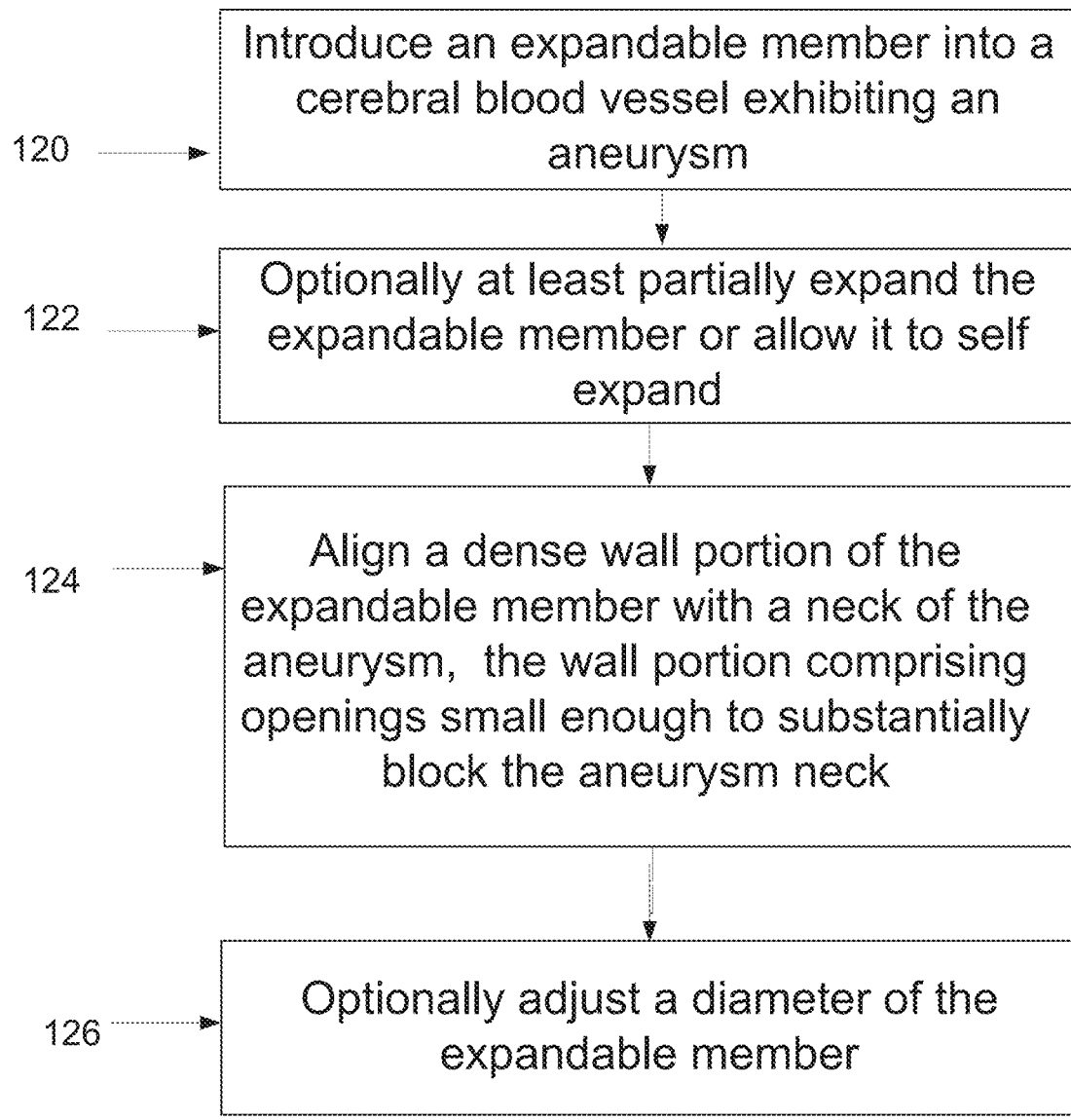

Referring now to the drawings, FIGS. 1A-1B are flowcharts of a detailed method (1A) and a general method (1B) of deploying an expandable member in a blood vessel exhibiting an aneurysm, according to some embodiments of the invention.

In some embodiments, a patient is diagnosed with a cerebral aneurysm, for example using angiography, imaging, and/or CSF analysis methods. In some embodiments, a device comprising an expandable member is introduced to the blood vessel (e.g. the middle cerebral artery) exhibiting the aneurysm, for example by a physician (100).

Optionally, the device is introduced through the femoral artery, and advanced through the vascular system, into the cerebral circulation, and into the blood vessel exhibiting the aneurysm. Alternatively, the device is introduced in an endonasal approach, and/or any other methods suitable for delivering the expandable member into the vessel, to a location of the aneurysm.

In some embodiments, the device comprises a delivery system, for example including a microcatheter and optionally an outer tube axially movable within the microcatheter, in which the expandable member is crimped during delivery, and at least one mechanism for modifying a diameter and/or length of the expandable member, for example as further described herein.

In some embodiments, optionally, the expandable member is at least partially expanded in the vessel (101). Optionally, the member is selectively expanded by the user. Additionally or alternatively, the member is configured to self-expand, for example when released from the outer tube.

Optionally, coiling of the aneurysm is performed (102). In some embodiments, a second coil-delivering microcatheter is inserted into the vessel. The coil-delivering microcatheter may be inserted prior to introducing of the device, simultaneous to introducing of the device (e.g. by passing the coil-delivering microcatheter in parallel to the microcatheter of the device through which the expandable member is delivered), and/or following deployment of the expandable member (e.g. by passing the coil delivering microcatheter through one or more openings of the deployed expandable member). Blood may clot around the coils within the aneurysm, potentially promoting sealing of the aneurysm.

When the expandable member is positioned within the vessel at the location of an aneurysm, in some embodiments, it is at least partially expanded. Optionally, the expandable member is expanded to a configuration in which at least a portion of the expandable member engages the walls of the blood vessel at the aneurysm location (103). Optionally, the expandable member is expanded to an extent in which the walls of the expandable member form circumferential contact with the vessel walls.

Additionally or alternatively, the expandable member is temporarily contracted and/or remains in the crimped state it was delivered in, for example to provide for a coil-delivering microcatheter to be positioned in the vessel along with the expandable member, e.g. by passing the microcatheter axially parallel to the expandable member, to be positioned, for example, between the expandable member and the vessel wall.

In some embodiments, the expanded member leans against vessel walls proximally and/or distally to a neck (may also be referred to as a base) of the aneurysm, such that at least a portion of a wall of the expandable member obstructs the aneurysm neck, reducing and/or preventing flow into and/or out of the aneurysm. Optionally, a rate of the flow into and/or out of the aneurysm is slowed down by the expandable member to a rate sufficient to enable a thrombotic reaction and/or scaffolding of the vessel wall tissue to take place. Additionally or alternatively, the expanded member leans against the vessel walls, obstructing the aneurysm neck to prevent one or more coils which have optionally been introduced into the aneurysm from protruding out of the aneurysm and into the vessel.

In some embodiments, the member comprises one or more openings through which blood can flow. In some embodiments, the expandable member is structured to allow non-radial flow, such as axial flow, through the vessel. In an example, the member comprises a braided structure formed of a plurality of meshed wires which define the openings therebetween. By allowing non-radial flow of blood, in some embodiments, at least a partial patency of the vessel is maintained and/or obtained and/or restored.

In some embodiments, a diameter and/or position of the expandable member, for example an axial position of the member in the vessel, are adjusted (104).

In some embodiments, a diameter of the expandable member is modified, i.e. increased or decreased by using a control mechanism, optionally operable from outside the body. In some embodiments, the control mechanism comprises applying axial force, for example by pushing and/or pulling a cable operatively coupled to the expandable member and/or delivery system or components thereof. In an example, the cable is coupled to a distal end of the expandable member and/or to an element such as a cup shaped element attached to the distal end of the member, and the cable can be axially pulled or advanced, for example by the user from outside the body, to move the distal end of the expandable member relative to the delivery system, such as relative to a distal end of an outer tube through which the expandable member is introduced. In some embodiments, axial manipulation of the cable expands a diameter of the member (for example when the cable is pulled on) and/or reduces a diameter of the member (for example when the cable is advanced distally) by actuating movement of the distal end of the member relative to the outer tube, such as relative to a distal end of the outer tube.

In some embodiments, the expandable member is delivered into the vessel in a collapsed, reduced diameter configuration. Optionally, the member self expands to an initial diameter when advanced out of the delivery tube, such as a microcatheter. The initial diameter may be, for example, 50% of the vessel diameter at the aneurysm location, 70% of the vessel diameter at the aneurysm location, 90% of the vessel diameter at the aneurysm location, and/or intermediate, larger or smaller percentages of the vessel diameter. In some embodiments, the member self expands into a diameter which is 5%, 20%, 45%, 70%, 85% or intermediate, larger or smaller percentages of a collapsed diameter of the expandable member. Optionally, the initial diameter to which the member self expands is preselected to match a vessel of a certain diameter. Alternatively, the member remains in a collapsed configuration until modified by the user. Additionally or alternatively, initial expansion is actuated by a user (e.g. in response to pulling on the cable), and self expansion follows the user actuated expansion, for example when the member is expanded into a preselected diameter. Some embodiments may include various combinations of user-actuated modifications (e.g. expansion and/or contraction) and self occurring modifications (e.g. expansion and/or contraction).

In some embodiments, the member is expanded to a diameter in which the walls of the member contact the vessel walls, but do not exert substantial pressure such as radial pressure onto the vessel walls. Optionally, an amount of radial pressure exerted by the walls of the expandable member onto the blood vessel walls is sufficient for obtaining hold of the expandable member by the vessel walls, preventing the member from being carried away from the aneurysm location by flow. By accurately controlling the extent of expansion of the member, over-sizing (i.e. expanding the member to a too large diameter which may apply unnecessary radial force onto the vessel walls) and/or under-sizing (i.e expanding or narrowing the member to a too small diameter which may not be effective to obstruct flow into and/or out of the aneurysm) may be reduced or prevented.

In some embodiments, the diameter is adjusted a plurality of times. Optionally, the diameter is adjusted after a visual indication of the position of the member (e.g. an axial and/or cross-wise position of the member relative the vessel) is obtained, for example by imaging such as fluoroscopy.

In some embodiments, the diameter is adjusted following initial deployment of the member in the vessel. Additionally or alternatively, the diameter is adjusted at later stages, for example when clotting has begun. Additionally or alternatively, the diameter is adjusted if a coiling procedure is performed, for example as further described herein, and coils are delivered into the aneurysm adjacent and/or through the expandable member. Additionally or alternatively, in cases in which the member is detached from the delivery system and positioned in the vessel for longer periods of time, or permanently deployed in the vessel, the member can be re-engaged with the control mechanism for re-adjusting its diameter. Additionally or alternatively, the diameter is adjusted according to a current clotting stage. In an example, a physician observes intra-aneurysm flow stasis and/or thrombosis, optionally immediately following deployment of the expandable member at the aneurysm neck, and modifies the diameter and/or length of the member accordingly.

In some embodiments, a position of the expandable member in the vessel, such as an axial position, is adjusted by the user. In some embodiments, the member is positioned by advancing or retracting the delivery tube such as the microcatheter in the vessel. Additionally or alternatively, the position is adjusted by advancing or retracting the member relative to the delivery tube, such as relative to the microcatheter. Additionally or alternatively, the positioning is adjusted by expanding and/or contracting the member, optionally repetitively, to move the member in rippling, wave-like movements.

In some embodiments, the expandable member is axially positioned in the vessel such that a central portion of the member extends across the aneurysm neck. Alternatively, a distal or proximal portion of the expandable member extends across the aneurysm neck.

In some embodiments, the expandable member blocks coils that were delivered into the aneurysm from exiting the aneurysm. This may be potentially useful in cases in which a dome diameter to neck diameter ratio of the aneurysm is relatively small, for example less than 2, less than 1.5, less than 1.8, or intermediate, larger or smaller ratios, in which the neck substantially does not produce a "bottle neck" effect, and the risk of coils passing through the relatively wide neck portion and out into the vessel is increased. Optionally, openings of the expandable member are small enough so as to prevent entangling of the coils (or ends of the coils which may extend externally to the aneurysm) with the wires of the expandable member.

In some embodiments, a wall portion of the expandable member slightly protrudes into the aneurysm neck, optionally producing an axial segment of larger diameter along the expandable member.

In some embodiments, the expandable member is detached from the delivery system. Optionally, the member is detached from the delivery system after an indication of initial flow stasis and/or thrombosis in the aneurysm is obtained, indicating that the selected position of the member is suitable for blocking coils from exiting the aneurysm and/or for restricting radial blood flow to and/or from the aneurysm. Optionally, the delivery system is retracted from the body, while the member remains deployed in the vessel. In some embodiments, one or more components of the delivery system are re-inserted into the vessel to re-engage the member and provide for modifying a diameter and/or position of the member, and/or for retracting the member away from the body. Alternatively, in some cases, the delivery system remains coupled to the expandable member.

In the exemplary general method of FIG. 1B, an expandable member is introduced into a cerebral blood vessel exhibiting an aneurysm (120), for example as further described herein. In some embodiments, the expandable member is at least partially expanded and/or allowed to self expand (122).

In some embodiments, a dense wall portion of the expandable member, for example defining a central axial segment of the expandable member, is a positioned to align at least 80%, 90%, 95%, 100% or intermediate, larger or smaller percentages of an axial length of the aneurysm neck, to substantially block the aneurysm (124). In some embodiments, blocking comprises reducing blood flow such as radial blood flow to and/or flow the aneurysm. In some embodiments, blocking comprises preventing one or more coils that were introduced into the aneurysm from exiting the aneurysm. In some embodiments, a diameter of the expandable member is adjusted (126). Optionally, the diameter is enlarged so that the expandable member engages the walls of the vessel and/or so that walls of the expandable member exert additional radial force onto the walls of the vessel, for example to anchor the member within the vessel. Alternatively, the diameter is contracted.

FIG. 2 illustrates a flow regime provided by an expandable member positioned to obstruct an aneurysm (2A), and radial expansion of an expandable member within a blood vessel to engage walls of the blood vessel (2B), according to some embodiments of the invention.

Figure 2A:
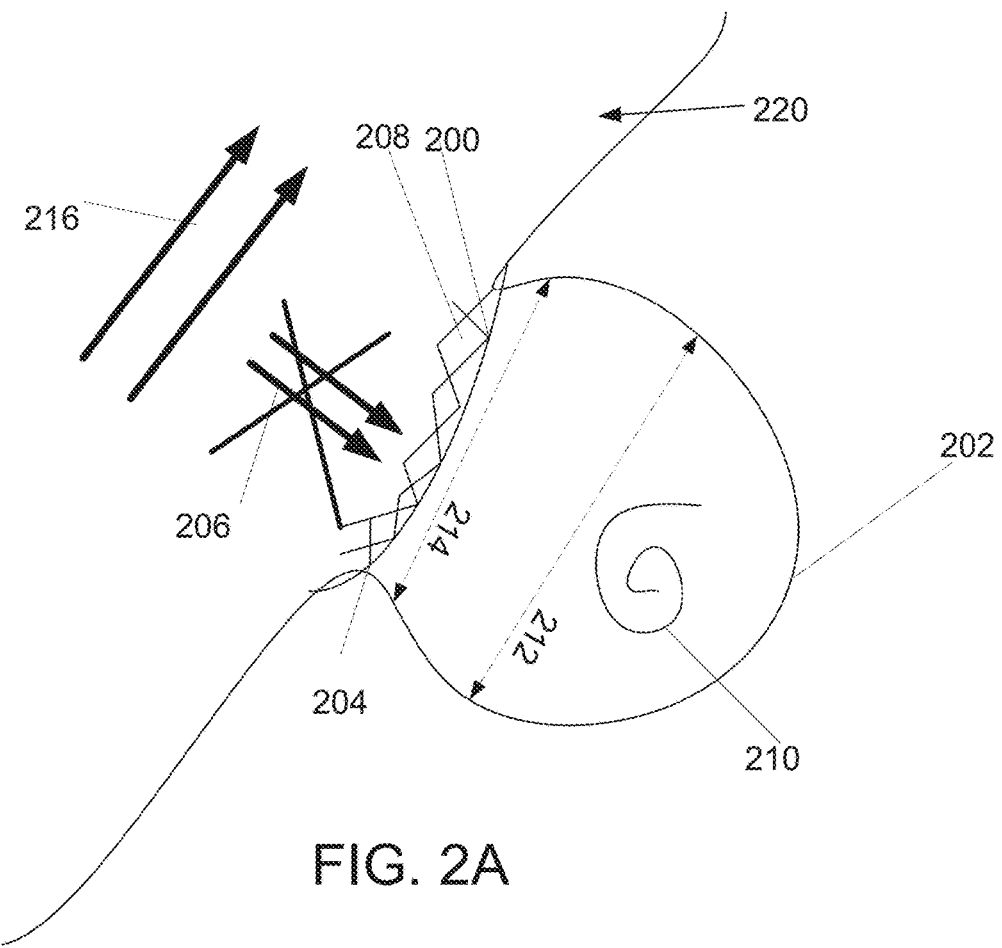
FIGS. 2A-2B illustrate a flow regime provided by an expandable member positioned to obstruct an aneurysm (2A), and radial expansion of an expandable member within a blood vessel to engage walls of the blood vessel (2B(1-3)), according to some embodiments of the invention.

In FIG. 2A, a wall portion 200 of the expandable member is shown to obstruct an aneurysm 202, in this example a saccular aneurysm comprising a substantially spherical shape. (Alternatively, in some cases, the treated aneurysm is a fusiform aneurysm, comprising a non spherical, optionally spindle shape, for example as further shown).

In some embodiments, wall portion 200 comprises a wire structure, optionally a braided mesh structure, defining openings 208 in between the wires.

In some embodiments, wall portion 200 extends across the neck 204 of aneurysm 202, substantially blocking radial flow 206 such as flow of blood into and/or out of the aneurysm. Optionally, flow 206 is obstructed due to openings 208 being small enough and/or arranged with respect to each other to define a high density wall portion through which flow cannot pass, or at least a substantial amount of flow is obstructed. In some embodiments, a certain flow volume is allowed to flow into and/or out of the aneurysm, as long as the flow rate is slowed down to rate sufficient for a thrombotic reaction to take place to eventually seal the aneurysm. For example, the flow rate is reduced to a rate lower than the coagulation rate of blood. In some embodiments, the coagulation dynamics of a specific patient are monitored, and the expandable member is adjusted and/or readjusted according to the flow dynamics. For example, the diameter of the member or one or more portions thereof may be reduced when sufficient sealing of the aneurysm is observed. Additionally or alternatively, the flow is slowed down enough to prevent rupture of the aneurysm. In some embodiments, flow dynamics are assessed using various techniques, such as injecting contrast media to be seen in the imaging system (x-ray, CT, angio-CT, MRI, etc.) to determine whether the position the member and/or extent of expansion of the member are suitable to sufficiently reduce a volume of the flow to and/or from the aneurysm. In some embodiments, a size of an opening 208 defined at wall portion 200 is small enough to prevent from one or more coils 210 which were introduced into aneurysm 202 from exiting the aneurysm. In an example, a cross sectional area of opening 208 ranges between 0.4 mm^2 to 2.5 mm^2, or intermediate, larger or smaller ranges. This may provide an advantage in cases in which a ratio between a diameter 212 of the aneurysm (for example at the widest portion of the aneurysm) and a diameter 214 of neck 204 is relatively small, for example smaller than 2, smaller than 1.8, smaller than 1.5 or intermediate, larger or smaller ratios, and a risk of coils 210 exiting the aneurysm is higher than cases in which the neck portion is narrower (i.e. comprises a smaller diameter) which is effective to stop the coils from entering the blood vessel.

In some embodiments, opening 208 comprises a cross sectional area which is smaller than a maximal cross sectional area of curled-up coil 210, in its non-planar form. Optionally, the cross sectional area of opening 208 is large enough to allow coil 208 to pass through when the coil is in a straightened, linear configuration, but small enough to prevent coil 208 from passing through when the coil has clumped into a non-linear form, inside the aneurysm. Optionally, opening 208 is large enough to allow a coil-delivering microcatheter to pass through, and small enough to prevent a coil that was released from the microcatheter and curled-up in the aneurysm from passing back through.

In some embodiments, coil 210 folds into a ball-like configuration. Optionally, a diameter of the ball-like configuration of the coil is larger than a maximal dimension of opening 208 (e.g. length, width, diameter and/or other dimension of opening 208, depending on the shape the opening which can be, for example, a rectangle, a circle, a square, a rhombus, an ellipsoid, a triangle and/or other cross sectional profile. Optionally, the shape of opening 208 changes in response to expanding or contracting the expandable member). A diameter of a ball-like curled up coil may range between, for example, 1 mm to 35 mm.

In some embodiments, a volume occupied by the curled up coil is large enough to prevent it from passing through opening 208, for example ranging between 0.5 mm^3 to 70 mm^3. Parameters that may determine the volume of the coiled up coil may include a length of the coil wire, for example ranging between 1-60 cm, and/or a thickness of the coil wire.

In some embodiments, the expandable member does not obstruct non-radial flow through the blood vessel, such as axial flow 216. Optionally, flow 216 passes through the proximal and distal ends of the member.

In some embodiments, the expandable member comprises a tubular configuration, having an opening at the distal and/or proximal end of the member. Additionally or alternatively, the proximal and/or distal end is tied up and/or otherwise crimped to a substantially closed configuration, for example forming an elliptic balloon like configuration when both of the ends are tied. In some embodiments, openings at one or both ends of the member are large enough so that even if the member is tied or crimped towards its end, flow such as axial flow 216 will still be allowed through. A potential advantage of providing for non radial flow such as axial flow through the member may include reducing the risk of clot formation and occlusion of the vessel.

In some embodiments, for example during deployment and/or expansion of the member, axial and/or radial flow are not obstructed by the member. Optionally, by controlling the expansion of the member, the member can be expanded to obstruct flow only at a certain time or stage of the procedure. For example, the physician may introduce the expandable member into the vessel, axially position the member at a desired location, for example aligned with the aneurysm neck, inject contrast liquid which can freely flow in the vessel and into and/or out of the aneurysm, to indicate their dimensions and/or location, and only then expand the member, optionally gradually, to a diameter suitable to obstruct the aneurysm. This may provide an advantage over a device such as a self expanding stent which upon deployment in the vessel immediately springs into a fully expanded position.

Figure 2B:
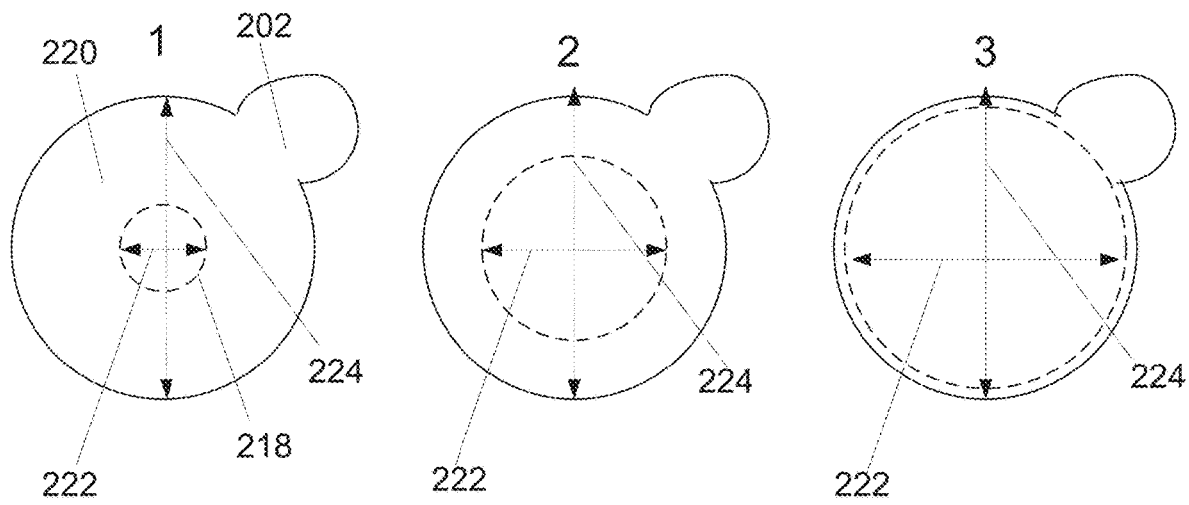
Figure 3:
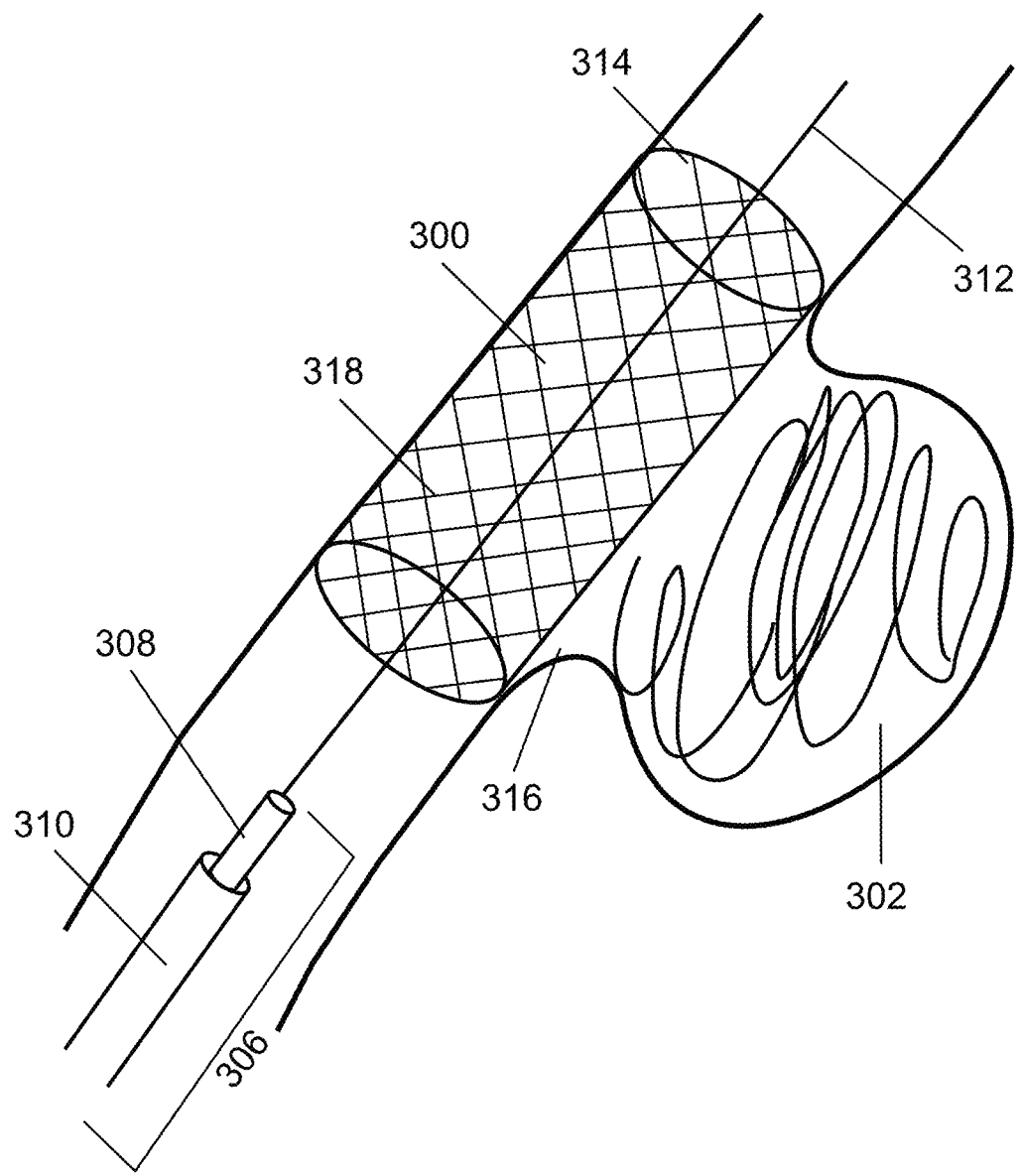
FIG. 3 is an exemplary configuration of an intravascular device comprising a tubular expandable member configured to at least partially obstruct an aneurysm neck, according to some embodiments of the invention.

FIG. 2B shows three exemplary expansion states of the expandable member 218, when viewed at a cross section of the blood vessel 220 exhibiting aneurysm 202. At 2B1, an exemplary initial, optionally collapsed configuration of member 218 is shown. Optionally, a diameter 222 of member 218 at this stage ranges between, for example, 20%, 30%, 50%, 60% or intermediate, larger or smaller percentages of vessel diameter 224. In some embodiments, the configuration shown at 2B1 is the configuration in which the expandable member is delivered into the vessel, for example using the delivery system. Alternatively, the configuration at 2B1 is a configuration which the expandable member self-expands to, for example upon being released from the delivery catheter. In FIG. 2B2, an exemplary intermediate expansion of member is shown, in which diameter 222 of member 218 extends to, for example, 60%, 70%, 80%, or intermediate, larger or smaller percentages of vessel diameter 224. In FIG. 2B3, an exemplary fully deployed configuration of the member is shown, in which the walls of member 218 are expanded to contact the vessel walls. Optionally, the walls of member 218 contact the vessel walls circumferentially. Alternatively, at least a portion of member 218 contacts the vessel walls in wall areas located adjacent aneurysm 202, for example proximally and/or distally and/or laterally (i.e. when viewed at a cross section of the vessel) to aneurysm 202.

It is noted that intermediate, larger and smaller expansion configurations of the expandable member are possible, and that in some embodiments the expandable member is configured for expanding to a plurality of diameters, such as 2, 3, 5, 9, 10, 15, 20 or intermediate, larger or smaller number of diameters.

In some embodiments, expansion and/or contraction of the member is continuous. Additionally or alternatively, expansion and/or contraction is performed in a step-wise manner. Optionally, a user selects a certain diameter out of a continuous range of diameters, and sets the member in that diameter.

In some embodiments, the device comprises a locking element for maintaining the member at the set diameter. In an example, the locking element is configured at a proximal end of the expandable member, and is designed to restrict movement of the push/pull cable (e.g. movement relative to the outer tube) to prevent unwanted changes in diameter and/or length of the member, and maintain the member, at least temporarily, in a fixed diameter. Additionally or alternatively, one or more locking elements, for example comprising a ratchet mechanism, a latch, a clutch and/or other elements suitable for controlling (e.g restricting) movement of the push/pull cable are configured in a handle of the device, positioned outside the body.

In some embodiments, the expandable member comprises varying diameters at different portions of the member. Optionally, the member at its relaxed state comprises non-homogenous diameters. Additionally or alternatively, portions of the member such as axial segments of the member can be expanded into different diameters. In an example, a longitudinal segment of the member which is aligned with the aneurysm neck may comprise and/or be expanded into a larger diameter than other portions of the member, allowing at least a portion of the member wall to slightly fit into the aneurysm neck.

FIG. 3 is an exemplary configuration of an intravascular device comprising a tubular expandable member 300 configured to at least partially obstruct flow into and/or out of an aneurysm 302, according to some embodiments of the invention.

In the figure shown herein, expandable member 300 is deployed in the vessel 304, at a position suitable to obstruct flow into and/or out of aneurysm 302 by bridging aneurysm neck 316. At least a portion of the wall of member 300 is aligned with aneurysm neck 316.

In some embodiments, for example as shown herein, member 300 can be detached from a delivery system 306, for example including an outer tube 308 through which member 300 is delivered, and a microcatheter 310 surrounding the outer tube. In the exemplary stage shown herein, delivery system 306 is retracted away in a proximal direction, while member 300 remains deployed in the vessel, held in place by the vessel walls.

In some embodiments, a push/pull cable 312 extends longitudinally within member 300. In the exemplary operational stage shown herein, cable 312 is no longer coupled to a distal end 314 of the member, and can be retracted away from the member and optionally out of the body.

In some embodiments, outer tube 308 is axially displaceable relative to microcatheter 310. Optionally, during positioning in the vessel, outer tube 308 can be advanced distally to microcatheter 310, to deploy member 300.

In some embodiments, for example during deployment, for example during detachment of the delivery system, member 300 is transformed from an elliptic, balloon like configuration, to a tubular configuration. Such transformation occurs, for example, when cable 312 and/or an element such as a cup crimping together a distal end of member 300 disengage the member, for example during retraction of the delivery system. Retraction of the delivery system may be performed in cases that involve permanent deployment or semi permanent deployment (e.g. deployment for a limited time period).

In some embodiments, member 300 comprises a braided mesh structure comprising a plurality of wires 318, for example between 16-100 wires, such as 16 wires, 24 wires, 48 wires, 80 wires or intermediate, larger or smaller number of wires. In some embodiments, a thickness of each wire, optionally being a diameter of a wire in cases in which the wire is circular in cross section, ranges between 25-125 micrometer, for example 30 micrometer, 50 micrometer, 85 micrometer or intermediate, larger or smaller thicknesses. In some embodiments, the wire comprises a rectangular cross section profile, an oval cross section profile, a flattened cross section profile and/or other cross sectional profiles.

Additionally or alternatively, member 300 comprises a different structure, for example a helical spring structure, a structure comprising a plurality of cage-like compartments, for example arranged as a bead chain, and/or other structures.

Figure 4:
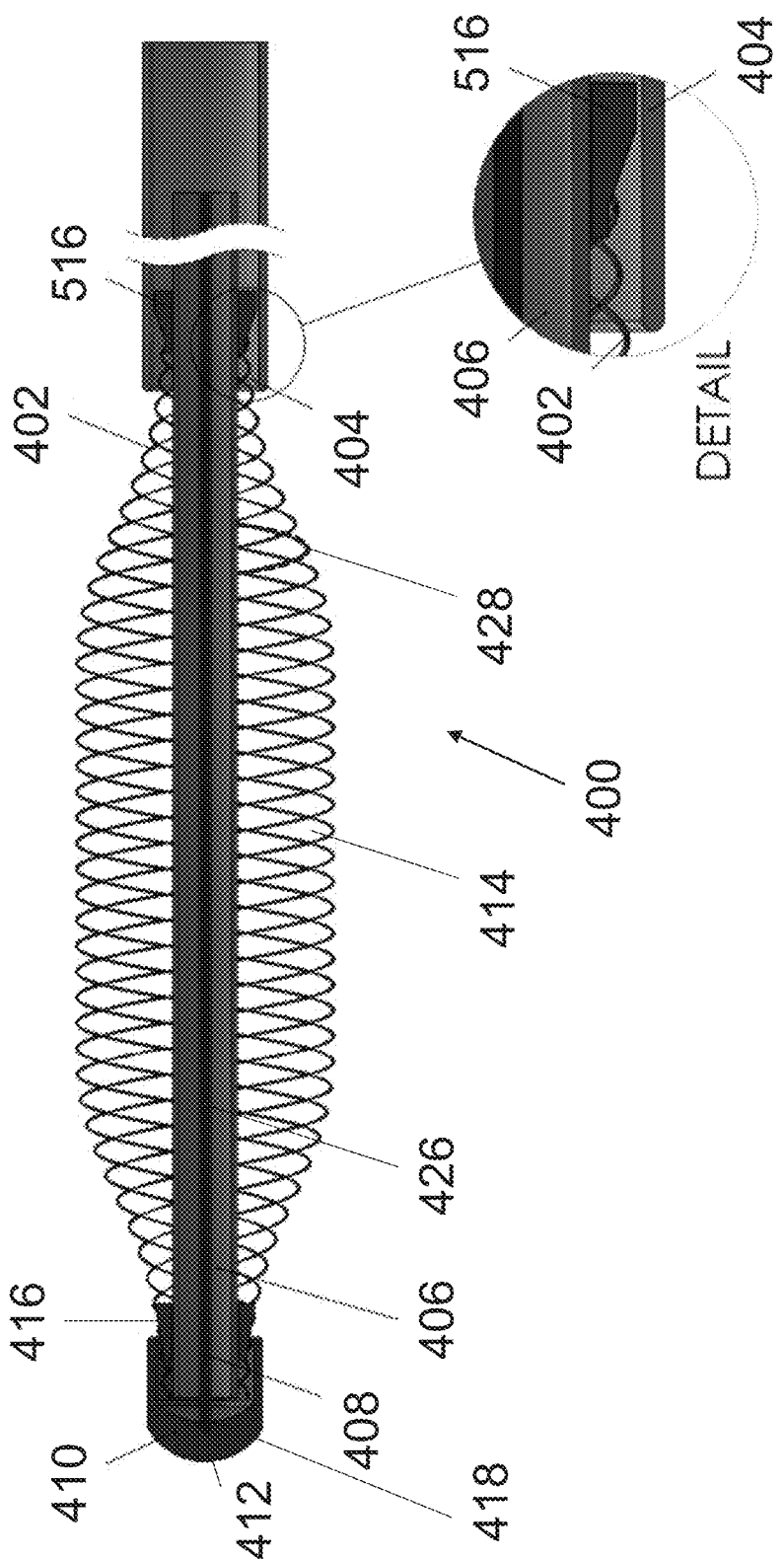
FIG. 4 is an illustration of a distal portion of a device comprising an expandable member, according to some embodiments of the invention.

FIG. 4 is an illustration of a distal portion of a device 400 comprising an expandable member, according to some embodiments of the invention.

The exemplary configuration in the figure shows expandable member 402 after it has been advanced distally, at least in part, from an outer tube 404. In some embodiments, outer tube 404 is sized and/or shaped to fit within a microcatheter (not shown in this figure).

In some embodiments, a securing tube 406 extends longitudinally within member 402, optionally extending further into outer tube 404. In some embodiments, securing tube 406 is axially movable (e.g. advanceable and/or retractable) within outer tube 404, for example by comprising a diameter smaller than a diameter of outer tube 404.

In some embodiments, a push/pull cable 408 extends longitudinally within an internal lumen 426 of securing tube 406. In some embodiments, cable 408 extends in a proximal direction beyond the securing tube and outer tube and optionally through the microcatheter to a distance in which it can be manipulated by a user from outside the body, for example using an operation handle (not shown in this figure).

In some embodiments, a distal end 412 of cable 408 is attached to cup 410. In some embodiments, cup 410 is long enough and/or wide enough to receive the distal portion of member 402 within it, accompanied by a distal end of securing tube 406 which is positioned over the distal portion of member 402 that is received within cup 410 to secure the member to the cup. Optionally, a distal portion of securing tube 406 presses the distal portion of member 402 against the walls the cup, providing lock-fitting to the cup.

In some embodiments, a diameter of cup 410 is at least 20%, 50%, 70% or intermediate, larger or smaller percentages smaller than the vessel diameter, such as to prevent occluding the vessel and provide at least partial patency. Exemplary dimensions of cup 410 include a diameter between 0.4 mm and 0.7 mm, between 0.2 mm and 0.5 mm, between 0.4 mm and 1 mm, or intermediate, larger or smaller ranges. In some embodiments, the cup is designed to be atraumatic, for example, a distal end of the cup may comprise of a soft material such as rubber or silicon so as to reduce damage to the tissue (e.g. the vessel walls). Optionally, the cup comprises a high friction material and/or coating, for example at the inner walls of the cup, which may assist holding the distal portion of member 402 in place. In some embodiments, cup 410 is perforated, for example comprising one or more holes 418 large enough to allow flow through.

Additionally or alternatively, a distal end of cable 408 is directly coupled to a distal end of member 402 in a removable connection.

Optionally, in a non detached configuration in which the delivery system is coupled to member 402, a distal portion of member 402 is received within cup 410, for example being crimped within the cup by a distal end of securing tube 406. Optionally, member 402 can be decoupled from cup 410, for example by pushing cup 410 distally to cause the crimped portion of the member within the cup to be released and expand radially outward. In some embodiments, the released portion expands outwardly to comply with a diameter of an expanded body portion 414 of member 402, optionally to contact walls of the vessel.

In some embodiments, a set of wedges 416 are rigidly attached to the outer wall of securing tube 406 at a distal end of the tube. Optionally, wedges 416 push the distal end portion of member 402 against the inner walls of cup 410 to temporarily fixate member 402 to the cup, for example during delivery and/or positioning of the member in the vessel.

In some embodiments, a second set of wedges 420 are rigidly attached to the outer wall of securing tube 406 a proximal end of the tube. Optionally, wedges 420 push the proximal portion of member 402 against the inner walls of outer tube 404 to temporarily fixate member 402 to a distal end of outer tube 404. Optionally, an axial distance between the sets of wedges 420 and 416 complies with an initial, optionally collapsed configuration length of the expandable member 402.

In some embodiments, when both the distal and proximal ends of member 402 are coupled to the cup 410 and the distal end of outer tube 404 respectively, movement of the distal end of member 402 relative to outer tube 404 can be obtained by axially pulling and/or pushing cable 408. Optionally, pulling cable 408 approximates cup 410 towards outer tube 404, thereby shortening a length 422 of member 402 and expanding its diameter; respectively, advancing cable 408 stretches member 402 distally, reducing a diameter of member 402.

In some embodiments, one or more radiopaque markers are incorporated in the expandable member and/or in the securing tube and/or in the outer tube and/or in the microcatheter, to visualize the components under imaging, such as under fluoroscopy. In an example, one or more radiopaque wires 428 are incorporated in the mesh of the expandable member. Optionally, the wire is made of tantalum. Alternatively, a wire is coated with a radiopaque material. Additionally or alternatively, markers in the form of an elongated line, ring, dot, and/or any other configuration are incorporated in the device.

In some embodiments, markers 428 are positioned to facilitate aligning a more dense wall portion or segment of the expandable member with the aneurysm neck. In some embodiments, the markers are configured at a periphery of the dense segment. In an example, if the dense segment is configured between two less-dense segments, the markers may align the borderline between the segments. In another example, markers are configured at one or more locations of the dense portion, for example at a center point of the dense portion. In some embodiments, one or more markers are positioned to indicate the proximal and/or distal ends of the member.

Exemplary materials from which the device components are made of may include: outer tube 404 comprising metal, plastic, or a combination thereof, having stiffness properties suitable for being passed within the cerebral vasculature (and/or other vasculature); push/pull cable 408 comprising metal; securing tube 406 comprising plastic, metal, or a combination thereof; expandable member 402 wires comprising a resilient material, optionally substantially elastic or super elastic alloy, such as nickel-titanium alloy or stainless steel, or a mixture of different metals (e.g. 15 Ni—Ti wires and Platinum).

In some embodiments, operation of the distal portion of the device, for example comprising axially pulling and/or pushing cable 408, retracting securing tube 406, retracting outer tube 404 and/or other actions are performed using a handle (not shown in this figure) configured outside the body and operatively coupled to the distal portion of the device. In some embodiments, the handle comprises scale marks for indicating a relative advancement/retraction of push/pull cable 408.

FIGS. 5A-5D illustrate deployment of an expandable member in a blood vessel exhibiting an aneurysm and optional retraction of the delivery system, according to some embodiments of the invention.

Figure 5A:
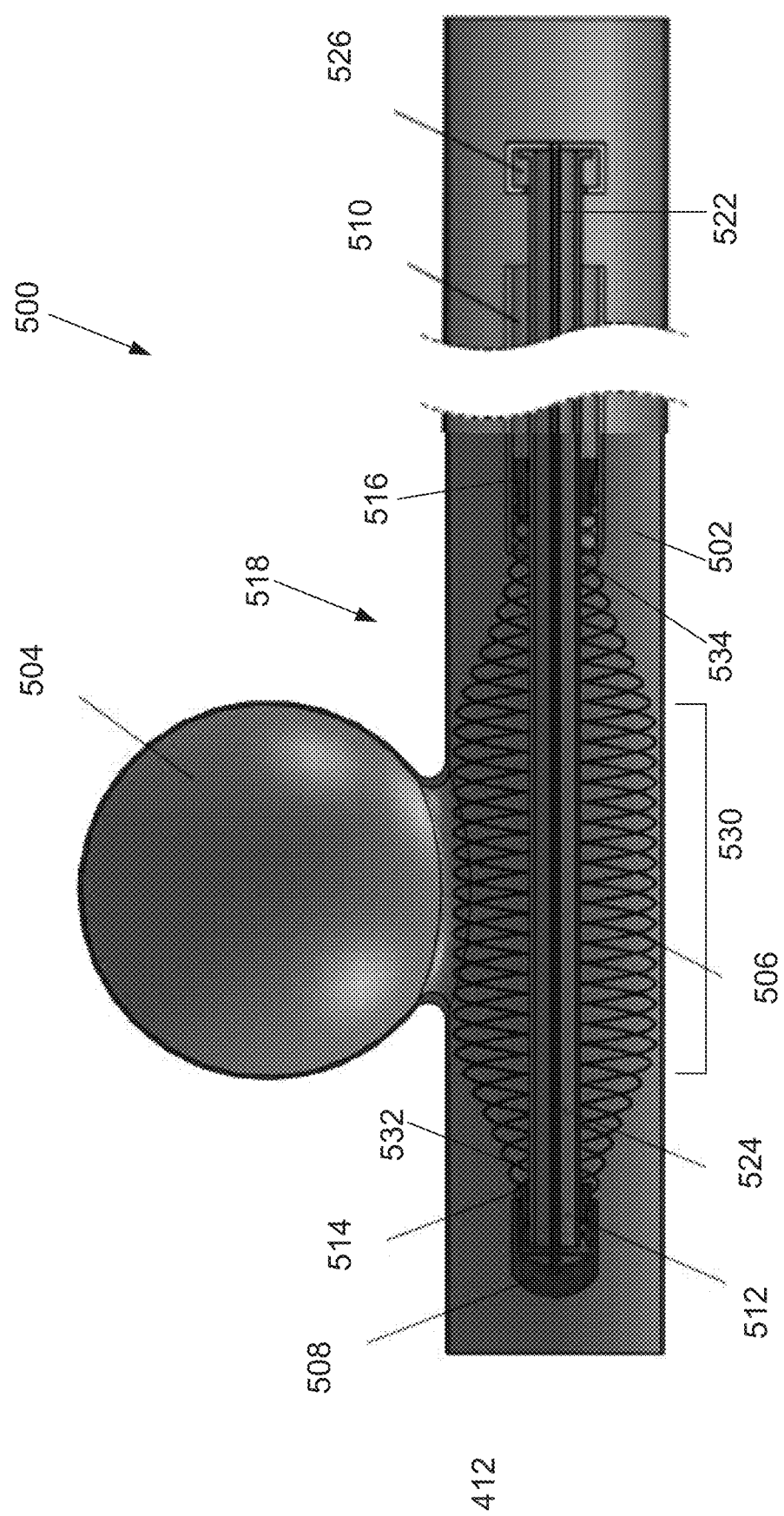

In FIG. 5A, a distal portion 518 of device 500 is shown within a blood vessel 502 exhibiting an aneurysm 504.

In some embodiments, device 500 is pre assembled by loading expandable member 506 onto the delivery system, outside the body. Optionally, loading is performed by the user, such as a physician. In some embodiments, the physician selects an expandable member from a kit comprising expandable members of various sizes and/or shapes and/or mechanical properties, for example according to the anatomy of the treatment site, the patient condition, and/or other parameters. Additionally or alternatively, loading of the expandable member is performed during manufacturing, and the physician operates the ready-to-use device. Optionally, operating comprises controlling the push/pull cable, for example during deployment, and/or detaching the expandable member from the delivery system, such as to permanently or temporarily deploy it in the vessel.

In some embodiments, the pre assembly procedure comprises one or more of: crimping the distal end 532 of member 506 into cup 508; positioning the proximal end 534 of member 506 into outer tube 510 while the securing tube 512 is threaded to a position in which it is proximally to a proximal end of outer tube 510; advancing securing tube 512 towards cup 508 such that wedges 514 lock the distal end 532 of member 506 to the cup 508, and wedges 516 lock the proximal end 534 of member 506 to outer tube 510.

In some embodiments, the assembly is delivered into the vessel, and expandable member 506 is positioned at the neck of aneurysm 504 and optionally expanded such that it obstructs flow to and/or from the aneurysm. Optionally, a microcatheter (not shown in this figure) is retracted.

In some embodiments, a proximal portion 522 of push/pull cable 524 is pulled and/or pushed relative to outer tube 510, optionally along with securing tube 512, to expand or contract member 506.

In some embodiments, pull/push cable 524 is coupled, for example at a proximal portion 522 of the cable, to securing tube 512 by a bridging element 526, extending for example at a substantially transverse direction to the longitudinal axis of cable 524.

In FIG. 5B, in an exemplary method of detaching member 506 from the delivery system, outer tube 510 and securing tube 512 are held in place while cable 524 is advanced distally, pushing cup 508 to release the crimped ends of member 506 from the cup. Optionally, outer tube 510 and securing tube 512 are held steady using one or more of a manual grip, a handle, and/or a torquer configured to hold both tubes.

Since a body 530 of expandable member 506 is caught, at this point, between the vessel walls, advancing of cup 508 will not or only slightly pull on the distal end 532 of member 506 until it is eventually released from in between wedges 514 and the walls of cup 508. In some embodiments, the released end of member 506 will expand to comply with body 530 of member 506 and engage the vessel walls.

It is noted that in some embodiments, member 506 remains coupled to the delivery system (comprising one or more of outer tube 510, securing tube 512, and/or cable 524) throughout the procedure. Detaching member 506 to temporarily or semi permanently deploy it in the vessel may be advantageous when treating a fusiform aneurysm, which may exhibit a very wide neck or no neck at all. When treating a fusiform aneurysm, delivery of coils into the aneurysm may be less effective than in a saccular aneurysm, due to the wide or non-existing neck of the fusiform aneurysm. In such cases, it may be advantageous to permanently position a flow diverting expandable member, for example as described herein, which comprises a geometry suitable to reduce or obstruct radial blood flow to and/or from the aneurysm.

Figure 5C:
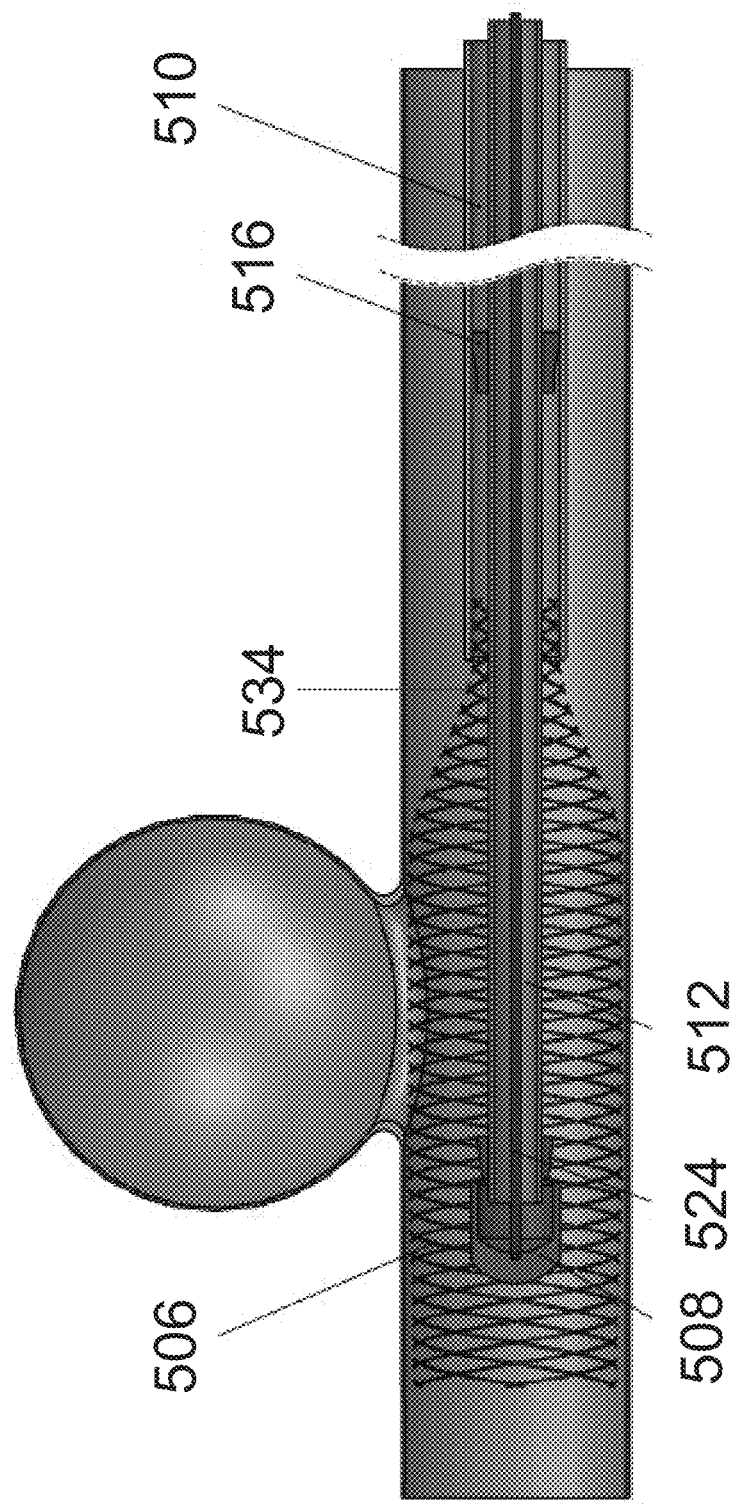

In FIG. 5C, outer tube 510 is held in place while cable 524 pulling along cup 508 are retracted proximally, engaging securing tube 512 so that all three components are retracted proximally. Optionally, at this point, the proximal set of wedges 516 that are externally mounted on securing tube 512 are pulled proximally along with the securing tube, releasing the secured coupling between a proximal end 534 of member 506 and outer tube 510. Proximal end 534 of member 506 remains loosely contained with outer tube 510.

Figure 5D:
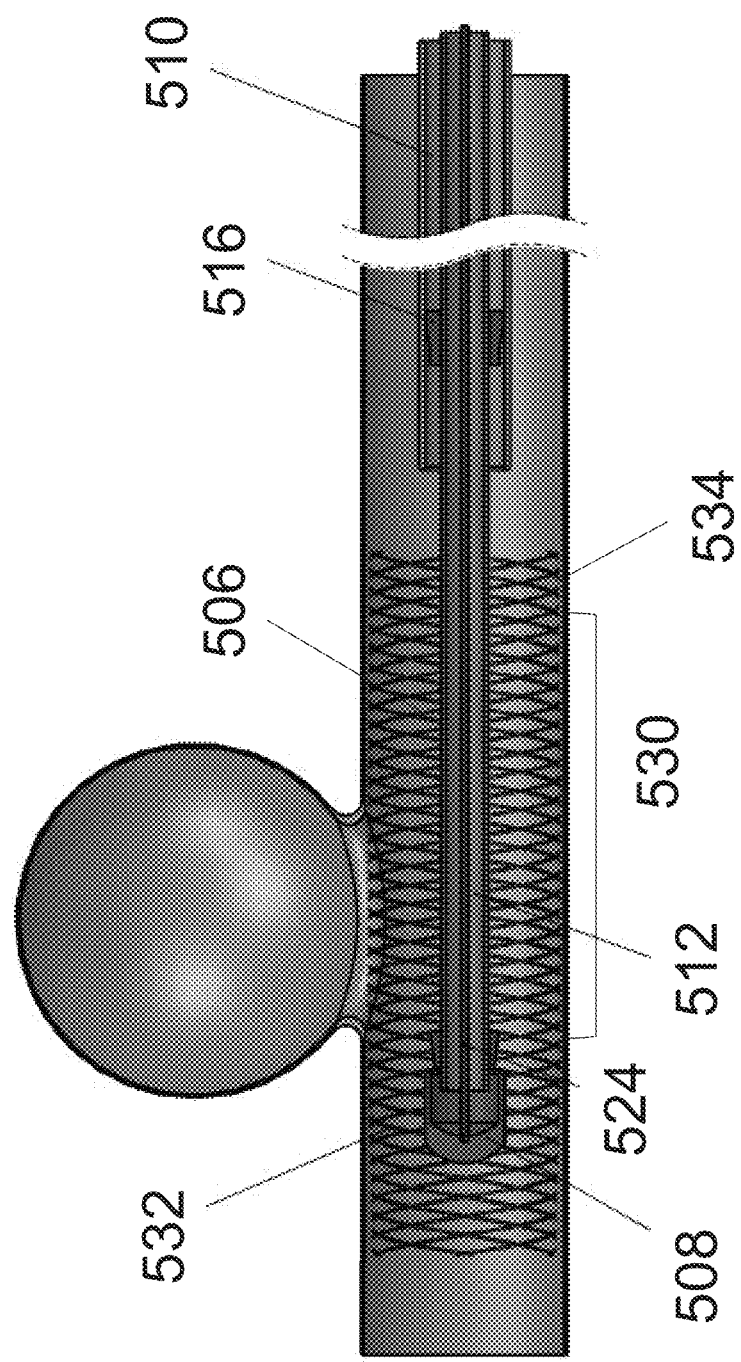

In FIG. 5D, the delivery system comprising one or more of outer tube 510, securing tube 512, cable 524 and/or cup 508 are further pulled in a proximal direction. Since body 530 and distal end 532 of member 506 are held by the vessel walls, proximal end 534 is released from outer tube 510, and optionally expands to comply with the rest of member 506 to engage the vessel walls.

Figure 6:
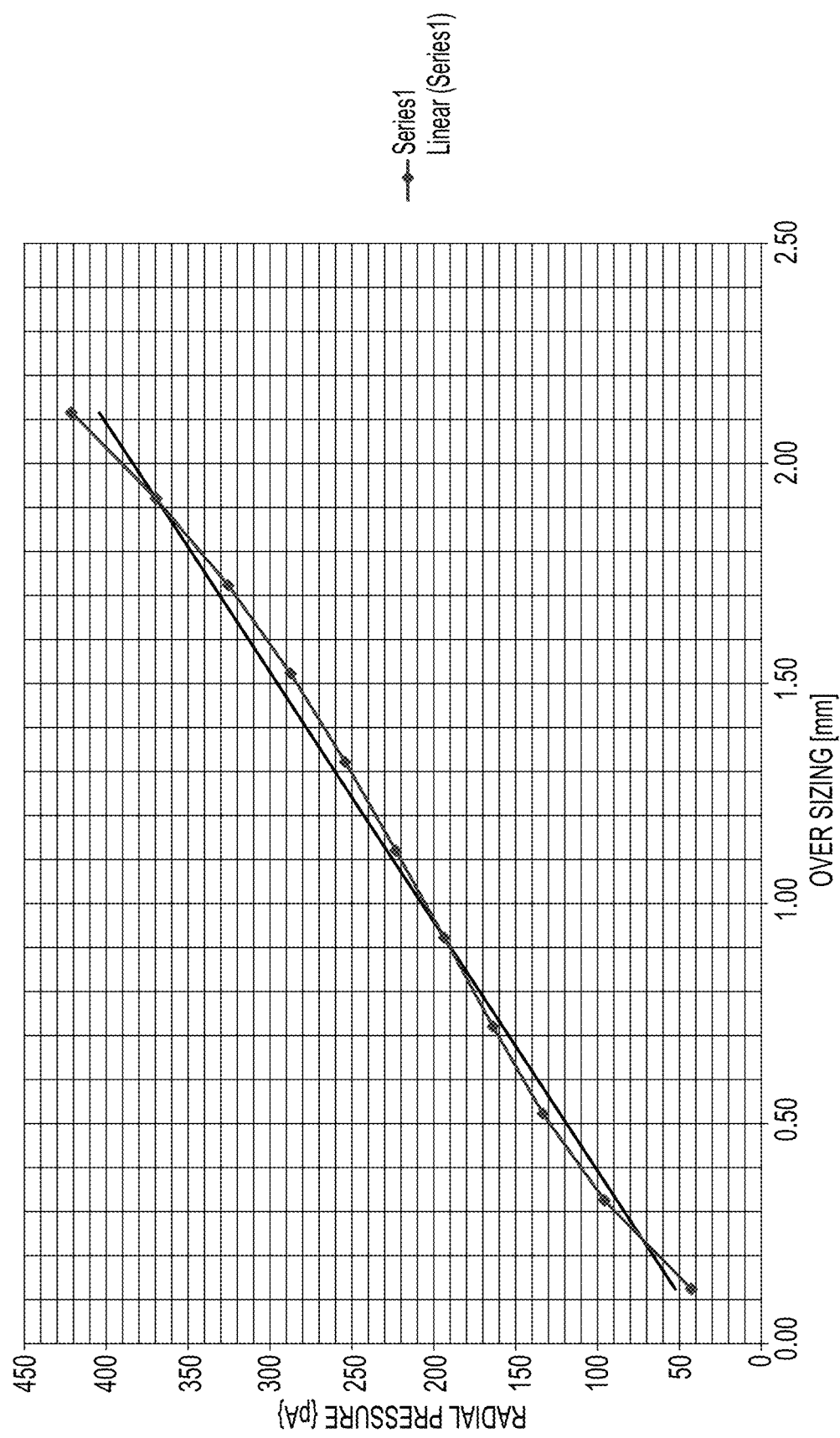
FIG. 6 is a graph of exemplary axial pulling distances effective to increase a radial pressure applied by the walls of the expandable member onto the walls of the vessel after the member has been expanded to contact the walls of the vessel (hereinafter "over sizing"), according to some embodiments of the invention.

FIG. 6 is a graph of exemplary axial pulling distances effective to increase a radial pressure applied by the walls of the expandable member onto the walls of the vessel after the member has been expanded to contact the walls of the vessel (hereinafter "over sizing"), according to some embodiments of the invention. Optionally, radial force applied by the walls of the expandable member onto the walls of the vessel is strong enough to anchor the expandable member to the vessel, for example preventing the member from unwanted axial movement in the vessel (which may occur, for example, as a result of strong blood flow).

In the exemplary graph shown herein, the horizontal axis indicates a distance (in mm) in which a distal end of the expandable member is pulled proximally by the push/pull cable, while the proximal end of the expandable member remains static. As a result of this axial pulling, a length of the expandable member is reduced while a diameter of the expandable member is increased, approximating the walls of the member close to or in contact with the walls of the vessel in which the member is positioned. The vertical axis indicates a radial pressure (in Pa units) applied by the walls of the expandable member onto the walls of the vessel. It can be observed that the amount of radial pressure increases in a substantially linear relationship to the pulling distance in which the distal end of the member is pulled proximally (assuming a proximal end of the member is fixed in place, and the distal end is pulled towards it). Alternatively, in some embodiments, the relationship between the shortening of the expandable member and the radial pressure is non-linear, for example it may be defined according to a predetermined function.

Figure 7:
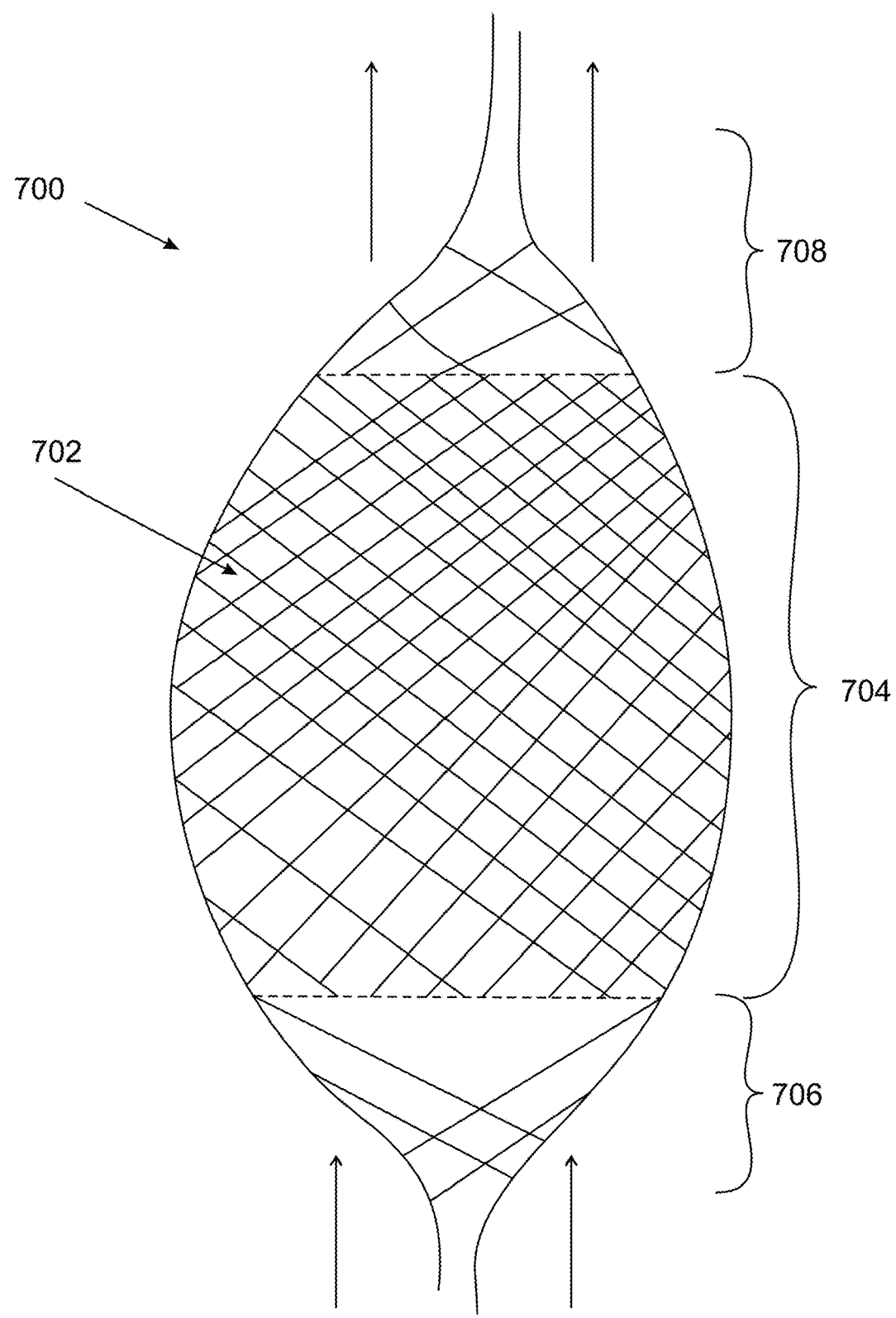
FIG. 7 shows an exemplary structure of an expandable member comprising openings of various dimensions, according to some embodiments of the invention.

FIG. 7 shows an exemplary structure of an expandable member comprising openings of various sizes, according to some embodiments of the invention.

In some embodiments, the wire arrangement of expandable member 700 defines a plurality of openings 702 of varying sizes. In an exemplary structure, a portion of member 700 such as a central section 704 comprises openings of smaller size defining a more dense section relative to the proximal section 706 and/or distal section 708, in which each of the openings comprises a larger size. A potential advantage of an expandable member comprising portions of varying densities may include obtaining a selected blood flow regime, for example by allowing increased flow volume through the larger openings (e.g. at the proximal and/or distal sections of the member) and reduced flow volume through the smaller openings (e.g. at a central section of the member). Optionally, central section 704 is positioned to obstruct the aneurysm neck, utilizing the smaller openings to slow or fully obstruct radial flow to and/or from the aneurysm, while axial flow and/or radial flow which is proximal or distal relative to the aneurysm is allowed to flow through sections 706 and 708, thereby potentially reducing interference with the natural flow in the vessel. Additionally or alternatively, the smaller openings of the central section are shaped and/or sized for blocking the passing of coils through, to prevent the coils from protruding and/or exiting the aneurysm.

Additionally or alternatively to axial segments of member 700 being formed with varying densities, circumferential portions of member 700 (i.e. of the walls of the member) may be formed with varying densities. For example, member 700 may comprise a lateral wall portion (e.g. a patch of the wall) which comprises a higher density than other portions, which can be rotationally oriented to be axially aligned with the aneurysm neck. Optionally, the dense wall portion and/or other portions of the member and/or components of the delivery system comprise radiopaque markers for indicating a current orientation of the member, so that a user can align the dense wall portion relative to the aneurysm neck.

In some embodiments, a higher density portion of the expandable member includes a larger number of wires as compared to a lower density portion. Exemplary structures of an expandable member comprising openings of different sizes and/or portions of different densities are further described herein, for example in FIGS. 16A-16B and 17A-17D.

Figure 8:
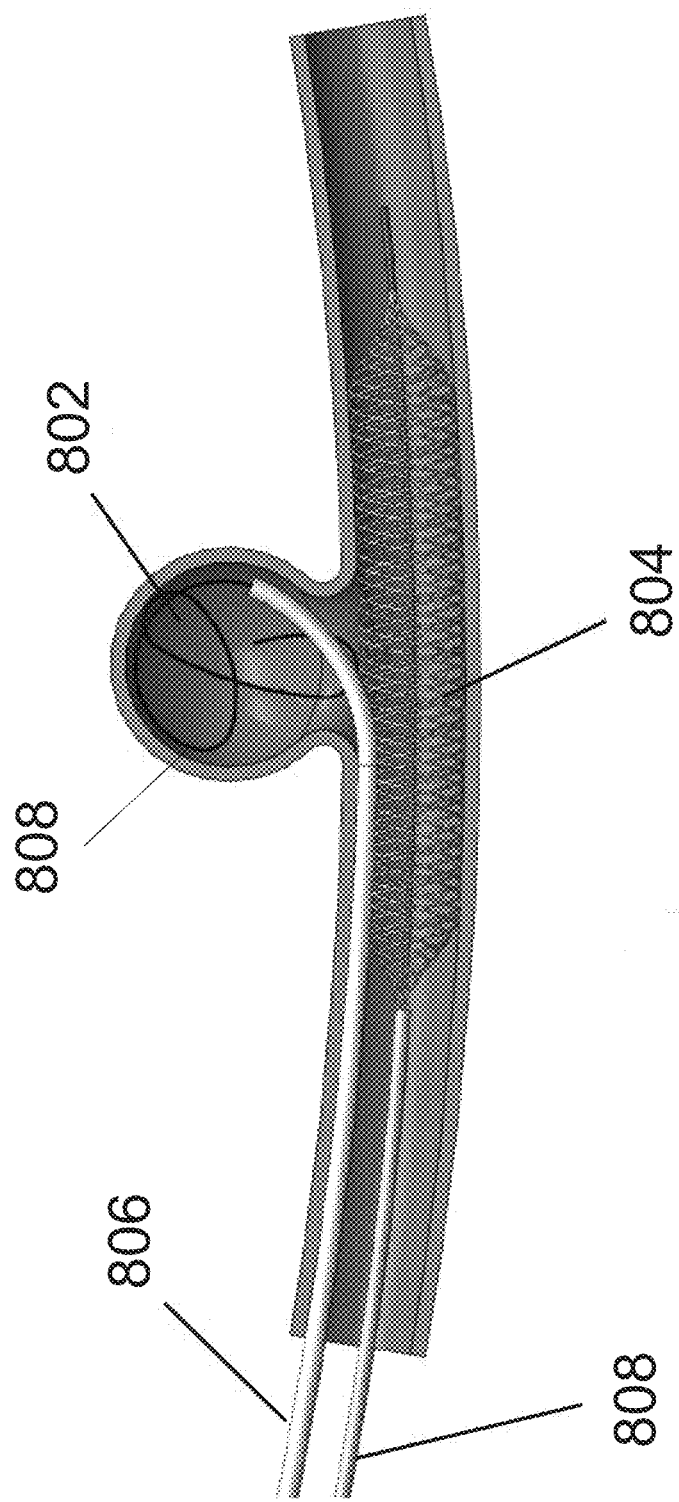
FIG. 8 illustrates coiling of an aneurysm parallel to deployment of an expandable member, according to some embodiments of the invention.

FIG. 8 illustrates coiling of an aneurysm parallel to deployment of an expandable member, according to some embodiments of the invention.

In some embodiments, one or more coils 800 are inserted into aneurysm 802, to induce clotting of blood that will isolate the aneurysm from circulation and close off the aneurysm. In some embodiments, coils 800 are packed within the aneurysm, acting as a barrier to the blood flow in addition the barrier provided by expandable member 804.

In some embodiments, coils 800 are introduced to the aneurysm through a delivery catheter such as a microcatheter 806. Optionally, a coil 800 is delivered in a flattened, linear configuration forced by the tubular lumen of the catheter, and curls-up to occupy a larger volume when released inside aneurysm 802. Optionally, coiling is performed using coiling devices and/or methods known in the art.

In some embodiments, expandable member 804 is introduced to the vessel before, after and/or in parallel to the insertion of coils 800. Optionally, microcatheter 806 through which the coils are delivered is advanced adjacent member 804, and inserted in part into the bulge of aneurysm 802 to deploy the coils.

In an exemplary embodiment, coil delivering microcatheter 806 is introduced to the aneurysm. Microcatheter 808, which comprises the expandable member 804, is then introduced the vessel. Expandable member 804 is deployed and axially aligned with the neck of aneurysm 802. Optionally, member 804 is expanded, for example until a side wall of member 804 engages microcatheter 806. Optionally, member 804 is expanded to apply radial force on microcatheter 806 which is sufficient to trap microcatheter 806 between the member and the vessel wall, and prevent its movement. At this point, in some embodiments, one or more coils are introduced through microcatheter 806 and into the aneurysm. Optionally, after the coils are deployed, microcatheter 806 is removed from the vessel, and member 804 may be further expanded to engage the vessel walls.

In some embodiments, microcatheter 806 is advanced into the aneurysm while member 804 is collapsed or configured at a partially expanded state (e.g. one in which it does not engage the vessel walls). Optionally, a distal portion of microcatheter 806 is advanced far enough into aneurysm 802 to prevent the coils from entangling with the wires of the expandable member. In a case in which the coils entangle with the expandable member, the member may be expanded and contracted, optionally repetitively, to lose hold of the coil. Once coils 800 are deployed in the aneurysm, member 804 may be expanded to engage the vessel walls, preventing the coils from exiting through the aneurysm neck and into the flow of blood in the vessel.

In some embodiments, coils 806 are delivered through microcatheter 808 through which the expandable member is delivered. Optionally, an internal tube (not shown in this figure), extending for example in parallel to the outer tube of the member, is used for the passing of coils through. This method may involve gradual deployment, for example the coils are introduced to the aneurysm first, and then the expandable member is positioned and/or expanded to obstruct the aneurysm.

Figure 9A:
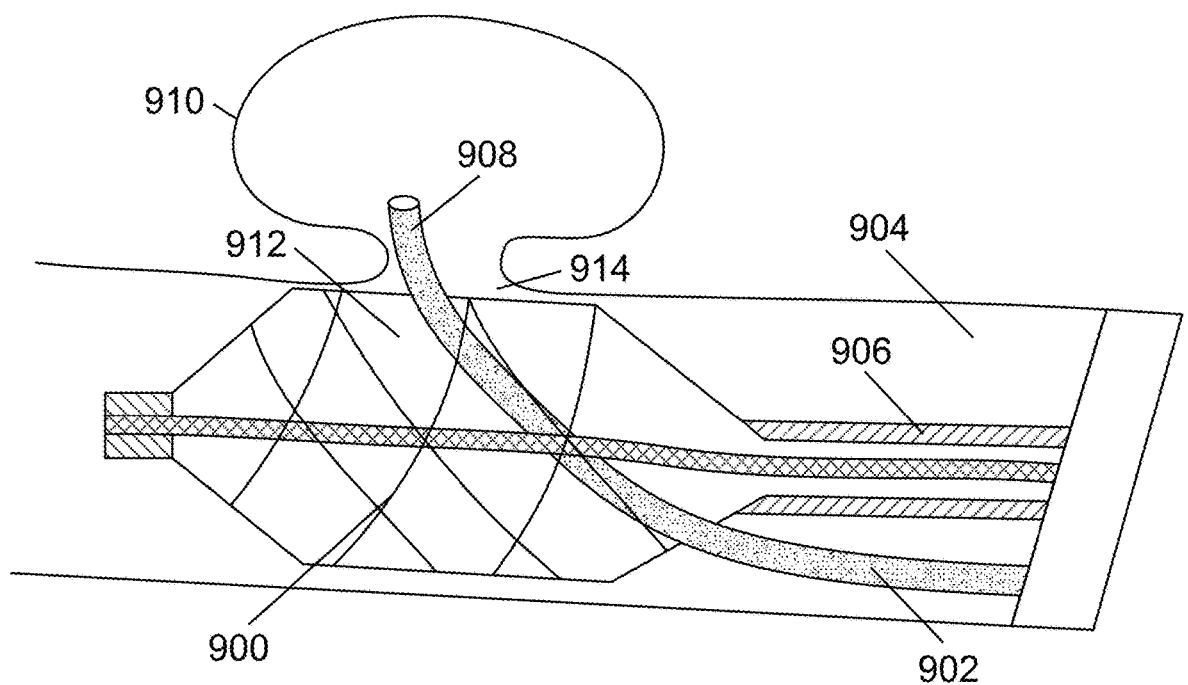
FIGS. 9A-9B illustrate coiling of aneurysm through a lumen of an expandable member, according to some embodiments of the invention.
Figure 9B:
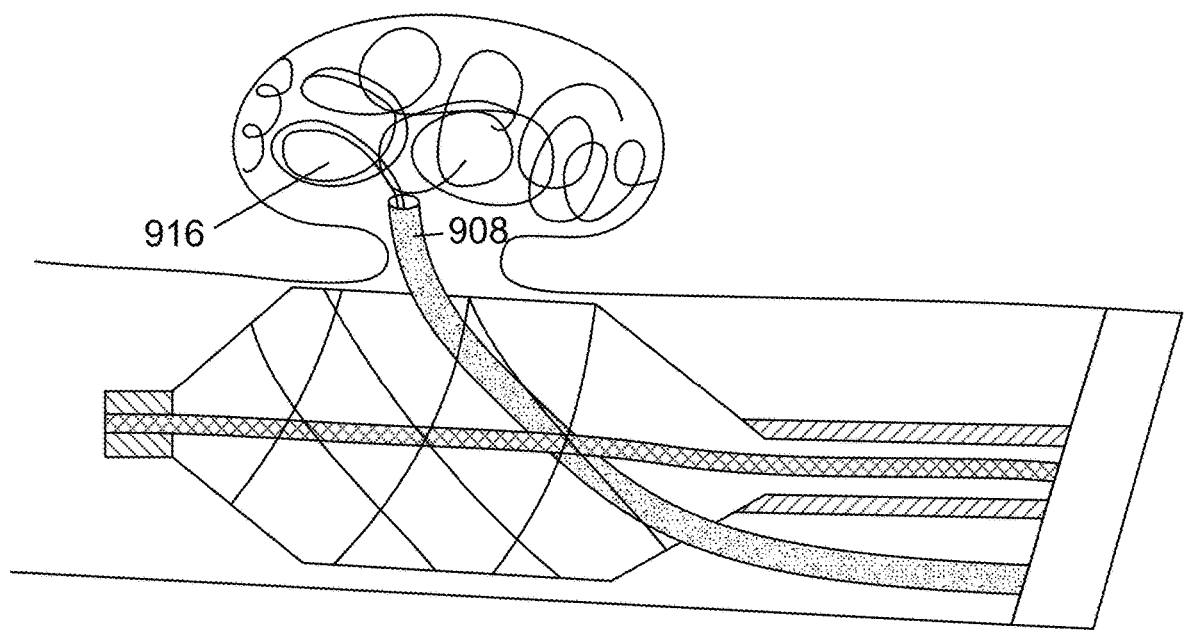

FIGS. 9A-9B illustrate coiling of aneurysm through a lumen of an expandable member, according to some embodiments of the invention. In some embodiments, coils are introduced through a volume of the expandable member 900. Optionally, for example as shown in FIG. 9A, a coil-delivering microcatheter 902 is introduced into the vessel 904, and passed in parallel to outer tube 906 and into a lumen defined by the walls of the expandable member. Coil-delivering microcatheter 904 is advanced until at least a distal portion 908 of the microcatheter is pushed through one of the openings 912 of the mesh of the expandable member, and located within aneurysm 910, for example within neck 914.

In some embodiments, for example as shown in FIG. 9B, one or more coils 916 are passed through microcatheter 902 and into aneurysm 910. Optionally, the coils are disposed in the microcatheter in a flat, linear configuration, and curl-up to occupy a larger volume when deployed in the aneurysm, for example to ball-like configuration.

In some embodiments, following deployment of the coils, microcatheter 902 is retracted proximally and optionally out of the body.

In some embodiments, a size of the one or more openings 912 of the expandable member is large enough to allow passing of at least the distal portion 908 of microcatheter 902 through, yet small enough to prevent the deployed coils 916 from protruding and/or exiting the aneurysm into vessel 904. Optionally, even though a diameter of a coil is smaller than a diameter of distal portion 908 of microcatheter 902 to enable delivery of the coil through the microcatheter, the coil, once deployed, may curl up to occupy a larger volume, and thus will not be able to pass back through opening 912.

Figure 10A:
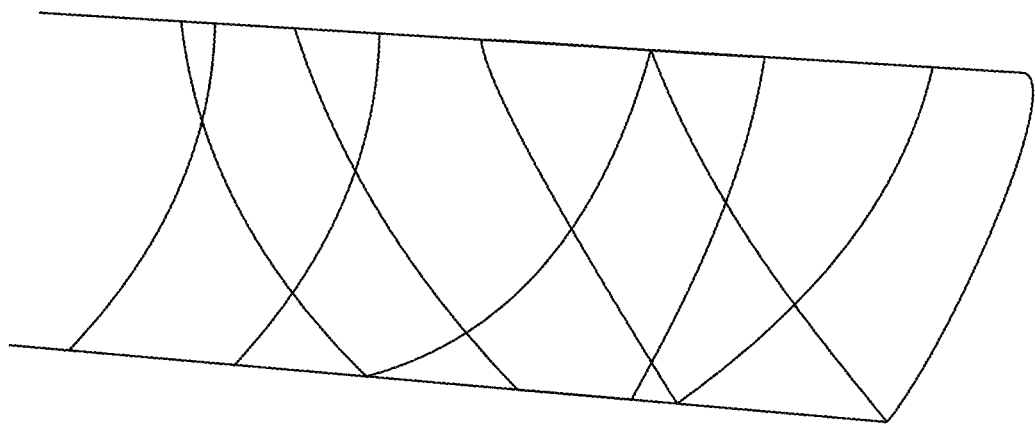
FIGS. 10A-10B are two exemplary structural arrangements of wires of an expandable member, according to some embodiments of the invention.
Figure 10B:
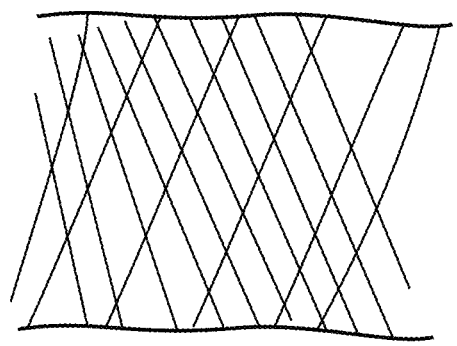

FIGS. 10A-10B are various wire structures of an expandable member, according to some embodiments of the invention.

In some embodiments, the braided wire structure comprises between 14-72 wires, such as 18, 24, 32, 64 or intermediate, larger or smaller number of wires.

FIG. 10A shows an exemplary 14 wire structure. FIG. 10B shows an exemplary 48 wire structure. In some embodiments, the wires are woven in a one over one structure; a one over two structure; a two over two structure; and/or other arrangement. A "one over one" structure may refer to an arrangement in which a single wire crosses over a second single wire; a "one over two" structure may refer to an arrangement in which a single wire crosses over two separate wires; and so forth.

In some embodiments, one or more parameters of the expandable member such as a diameter of the member (e.g. maximal and/or minimal diameters), a number of wires, the wire diameter, the wire arrangement (e.g. angles formed between crossing wires) and/or other parameters are selected to provide for positioning the expandable member at a bend or otherwise curved portion of a vessel, and/or at a junction between vessels. In an example, a wire of reduced diameter will be more flexible in comparison to a thicker wire, and may provide the flexibility needed for the member to adapt to the anatomical shape of the vessel at a curve.

Figure 11:
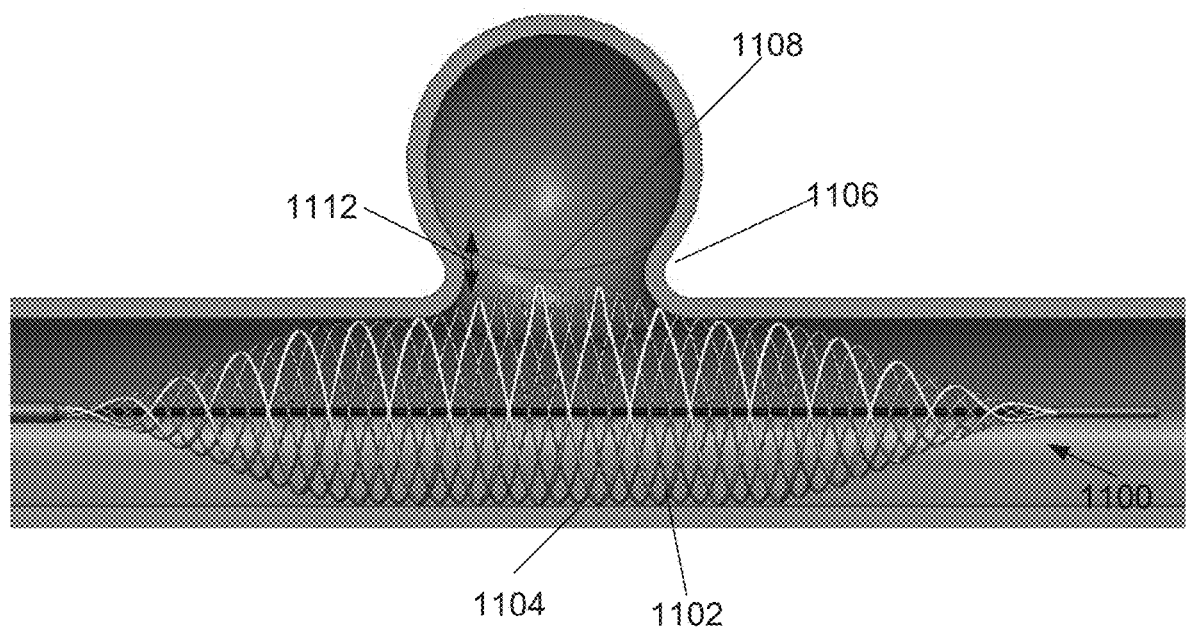
FIG. 11 illustrates an expandable member configured to fit, at least in part, into an aneurysm neck portion, according to some embodiments of the invention.

FIG. 11 illustrates an expandable member configured to fit, at least in part, into an aneurysm neck, according to some embodiments of the invention.

In some embodiments, a structure of expandable member 1100 is suitable for plastic and/or elastic deformation, to provide the shaping properties needed for fitting in the vessel, and, in some embodiments, to slightly protrude into the aneurysm neck, such as to obtain a closer alignment with the neck and restrict the flow. In some embodiments, expandable member 1100 comprises a combination of shapeable elements, such as annealed or semi-annealed wires 1102, and elastic or super-elastic elements, such as wires 1104. Optionally, wires 1102 and wires 1104 are formed of a similar material, such as nitinol, processed using different methods, such as thermal treatment. Alternatively, wires 1102 are formed of a material different than wires 1104.

In some embodiments, the annealed wires are interwoven with the elastic wires. Optionally, a number of the annealed wires is selected to provide sufficient resistance of the expandable member to deformation when a force (e.g. pulling or pushing force) under a certain threshold is applied, and to succumb to a force (e.g. pulling or pushing force) over a certain threshold, such as to enable expansion or contraction of the member.

In some embodiments, the yield strength of the elastically deformable members is at least 3 times, 5 times, 7 times or intermediate, larger or smaller number higher than the yield strength of the plastically deformable members. In an example, the expandable member is formed of annealed metal wires exhibiting a yield strength of approximately 200 MPa, interweaved with nitinol wires exhibiting a yield strength of 1200 MPa.

In an example, a ratio between the plastically deformable elements, such as annealed wires, and elastically deformable elements, such as nitinol wires, ranges between, for example, 5%-40% plastically deformable elements and 60-95% elastically deformable elements, or intermediate, larger or smaller ranges. In another example, all the wires forming the expandable member are annealed or semi-annealed.

In some embodiments, annealed wires 1102 are plastically deformed in response to applied stress, for example during expanding of the expandable member and/or during contraction of the member, and are configured to maintain the member in a selected configuration, for example a selected diameter. In some embodiments, by maintaining the expandable member in a selected shape, the annealed wires reduce the need for externally controlling the member (e.g. by applying constant tension to the pull cable) to assure that a certain configuration is maintained over time.

A potential advantage of an expandable member comprising a combination of annealed wires and elastic wires may include the ability to conform to the vessel anatomy of a patient. Optionally, the shapeable expandable member fits a small distance 1112 within the aneurysm neck. Optionally, the close fitting of the expandable member reduces gaps that may form between the vessel walls and the walls of the expandable member, for example at the base corners 1106 of the aneurysm neck.

In some embodiments, due to spreading of a wall portion 1108 of the expandable member over a larger area at the aneurysm neck, the openings defined between the wires at wall portion 1108 may be different in size (e.g. larger than) as compared to openings at one or more other portions of expandable member.

Figure 12:
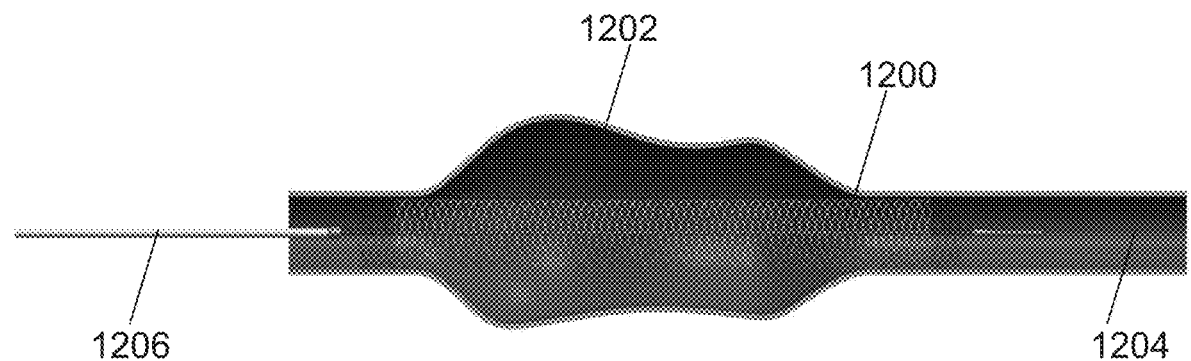
FIG. 12 is an exemplary configuration of an intravascular device comprising an expandable member structured to divert flow at an aneurysm location, according to some embodiments of the invention.
Figure 13:
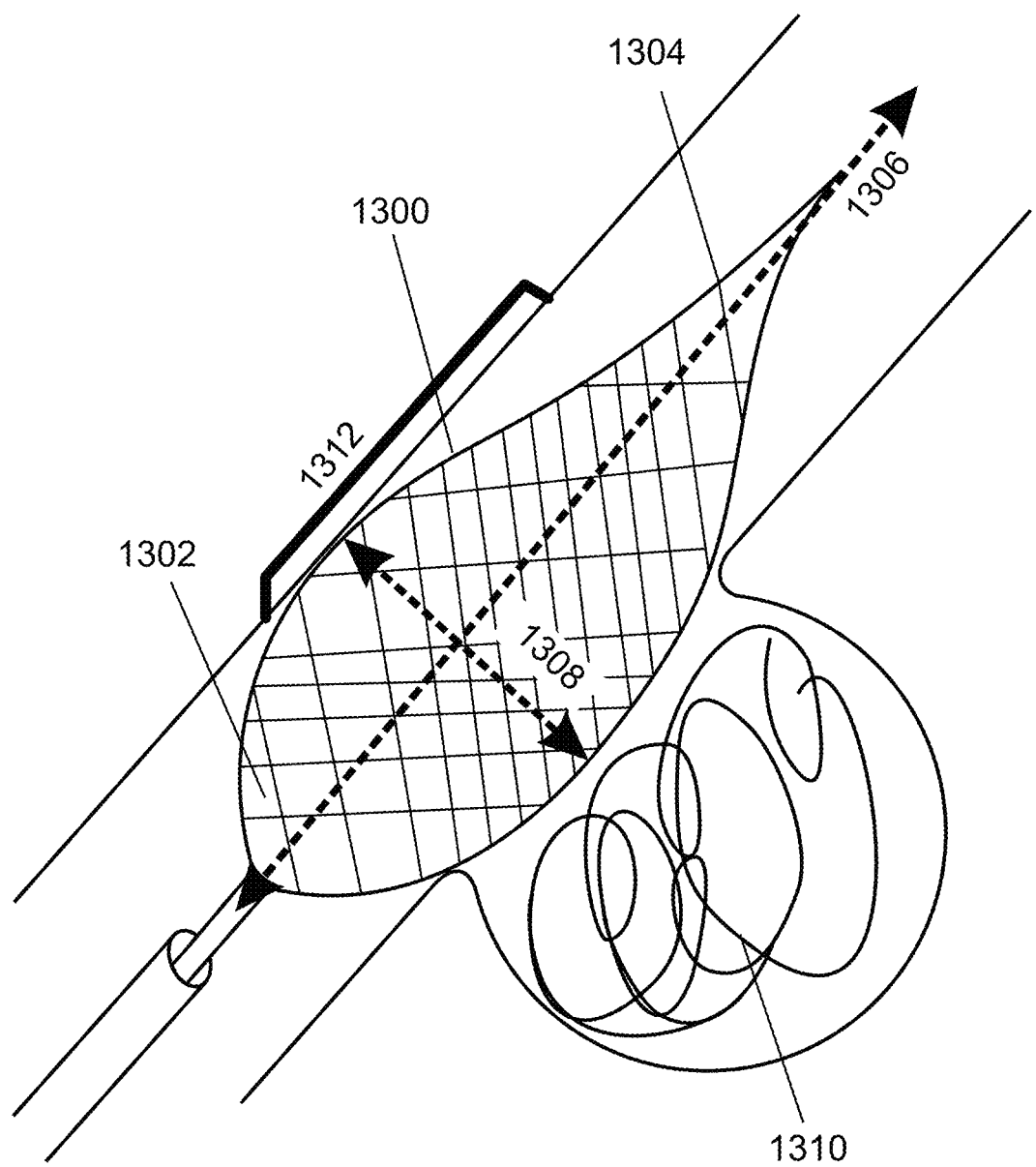
FIG. 13 is an exemplary configuration of an intravascular device comprising a balloon shaped expandable member configured to at least partially obstruct an aneurysm neck, according to some embodiments of the invention.

FIG. 12 is an exemplary configuration of an intravascular device comprising an expandable member structured to divert flow at an aneurysm location, according to some embodiments of the invention.

In some embodiments, expandable member 1200 is structured to act as a flow diverter, for example by comprising at least a portion in which the wires are arranged in a configuration which is effective to redirect flow, such as radial flow, to flow in a different direction, such as longitudinally along the vessel. Optionally, openings defined between the wires are small enough to produce a barrier, causing the radially outward and/or inward flow (e.g. relative to the walls of expandable member) to change path and to flow in a diverted direction, such as an axial direction.

In the exemplary embodiment shown in the figure, flow diverting expandable member 1200 is positioned to extend along the length of a fusiform aneurysm 1202, which in some cases is located on diametrically opposing sides of vessel 1204.

A fusiform aneurysm may vary in radial extent and/or length, and in some cases, the expandable member may be preselected according the shape of the aneurysm. Additionally or alternatively, dimensions of the expandable member may be adjusted in vivo to match the shape of the aneurysm In some embodiments, one or more parameters of the expandable member are selected, for example prior to insertion into the body, according to the observed shape and/or size of the aneurysm, and/or according to the curvature and/or diameter of the blood vessel. Such parameters may include, for example, a length of the member, a maximal diameter of the member, a size of the openings of the member, and/or other parameters. In an example, a conical expandable member, for example tapering towards its distal end, is selected to treat a longitudinally extending fusiform aneurysm in a blood vessel segment that tapers in a similar direction.

In some embodiments, member 1200 is deployed in the vessel and detached from its delivery system 1206. Optionally, member 1200 is left in the vessel for a desired time period such as. In some embodiments, the time period is predefined. Alternatively, the time period is determined based on progress, for example based on an assessment of the healing stage of the aneurysm.

In some cases, tissue grows on the internal and/or external sides of the walls of member 1200 (e.g. endothelium and/or neo-intima tissue.

In some embodiments, the balloon-like member 1300 expands to have a first, larger diameter at a central portion 1312, which decreases in size towards proximal end 1302 and/or towards distal end 1304, forming conical profiles at one or both of the ends.

In some embodiments, expandable member 1300 is symmetric, for example relative to the longitudinal axis 1306 and/or to the transverse axis 1308 of the member. Alternatively, member 1300 is asymmetric, for example comprising a first portion on one side of axis 1306, for example corresponding with the side of the vessel wall in which aneurysm 1310 is located, which expands to a radial distance larger than a radial distance to which a second portion of the member configured on the opposite side of axis 1306 expands. A potential advantage of a asymmetric geometry of the expandable member may include selectively obstructing or disrupting flow at certain vessel portions, for example at the aneurysm neck, and reducing interference with flow at other vessel portions, for example at vessel areas opposite the aneurysm.

Figure 14:
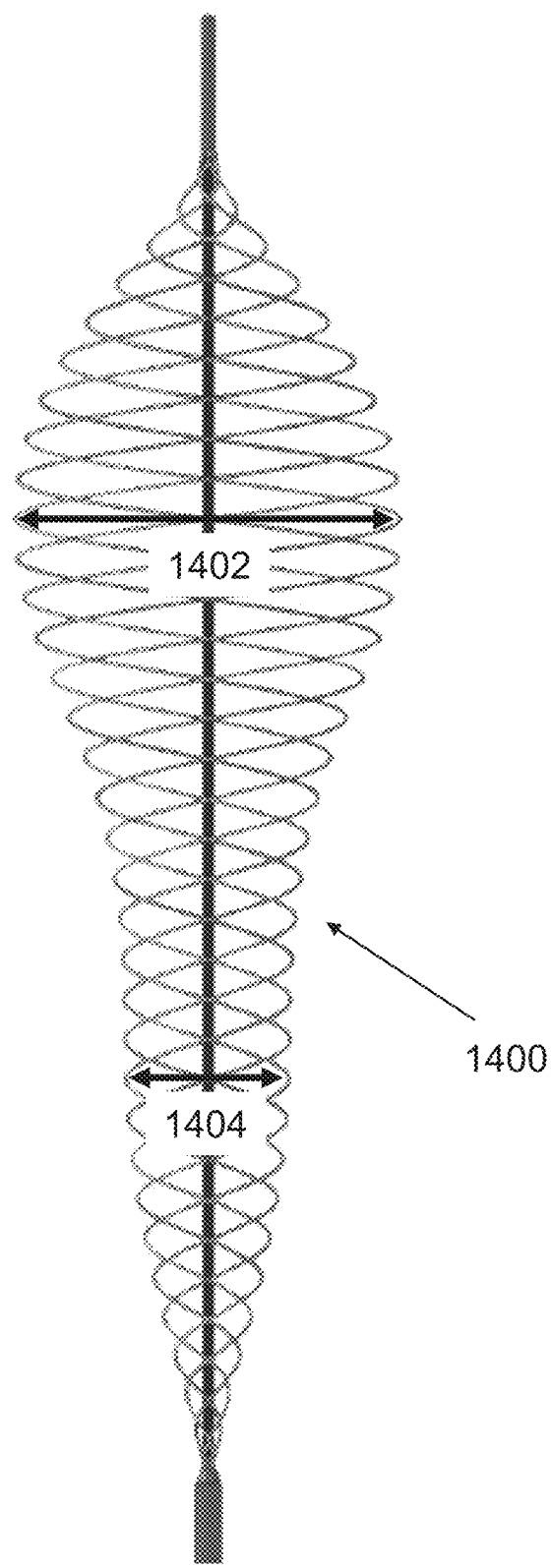
FIG. 14 illustrates a non-tubular expandable member configured to expand to varying diameters at different portions of the member, according to some embodiments of the invention.

FIG. 14 illustrates a non-tubular expandable member 1400 configured to expand to varying diameters at different portions of the member, according to some embodiments of the invention. In an example, the expandable member comprises a longitudinal segment which is configured to expand to a diameter 1402 larger than a diameter 1404 of a different longitudinal segment of the member. In an example, diameter 1402 is 10%, 30%, 60%, 85% or intermediate, larger or smaller percentages larger than diameter 1404.

It is noted that a configuration as shown herein may also be suitable for the treatment of other vascular conditions.

In some embodiments, the expandable member is pre-shaped, for example during manufacturing, to comprise different diameters at different portions. Alternatively, the expandable member comprises an initial homogenous profile, which is then adjusted (ex-vivo and/or in vivo) to form a structure with different diameters at different portions.

Figure 15A:
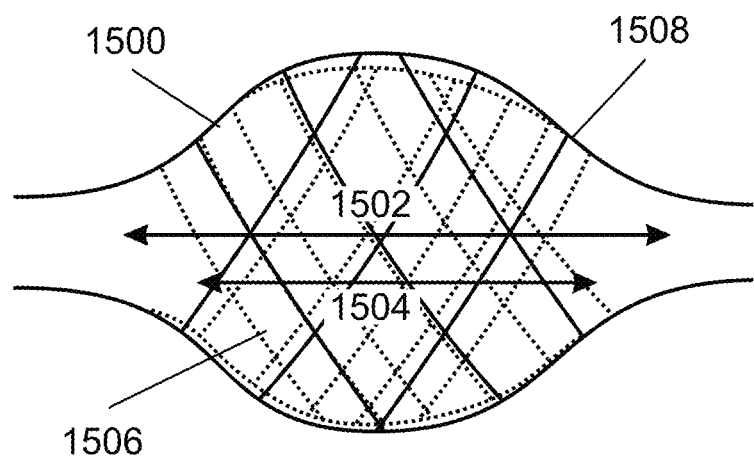
FIGS. 15A-15B illustrate an expandable member comprising a "cage over cage" structure, according to some embodiments of the invention.
Figure 15B:
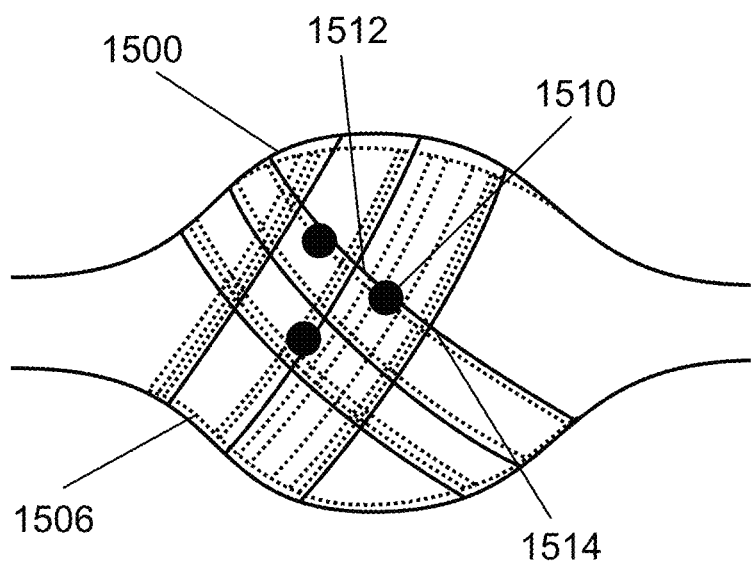

FIGS. 15A-15B illustrate an expandable member comprising a "cage over cage" structure, according to some embodiments of the invention.

In some embodiments, an expandable member comprises a "cage over cage" structure, for example comprising two wire mesh cages, optionally coaxial relative to each other. In some embodiments, a first outer cage 1500 comprises a relaxed length 1502 longer than a relaxed length 1504 of the second inner cage 1506. Optionally, relaxed length 1504 is between 50-75% of relaxed length 1502 of the outer cage. In some embodiments, inner cage 1506 extends only along a central portion of outer cage 1500.

In some embodiments, the cages are positioned with respect to each other such that a selected density of the over-layered openings is obtained. Optionally, the openings of cage 1500 overlap with the openings of cage 1506. Alternatively, the openings of cage 1500 only partially overlap or do not overlap with the openings of cage 1506, increasing the density. Optionally, the openings overlap at some portion of the cages, for example at proximal and/or distal portions of the cages, such to allow blood to flow through substantially without interfering with the flow, and do not overlap at other portions of the cages, for example at a central portion which may positioned at the aneurysm neck to obstruct it.

The figures shown herein illustrate two exemplary coupling arrangements between the inner and outer cages.

In FIG. 15A, the cages are coupled by an oversizing mechanism, in which inner cage 1506 self-expands into a relaxed diameter larger than a relaxed diameter of outer cage 1500. The walls of inner cage 1506 press radially outwards against the walls of outer cage 1500, thereby maintaining a friction based coupling between the cages. In some embodiments, the coupling reduces radial gaps between the inner and outer cages. Optionally, the coupling allows axial sliding movement of the cages relative to each other. In some embodiments, the cross sectional profile of outer cage 1500 narrows down (i.e. decreases in diameter) towards the proximal and/or distal ends of the member, and the narrowing 1508 acts as a stop which limits axial movement of inner cage 1506 relative to outer cage 1500, for example preventing inner cage 1506 from sliding towards the proximal and/or distal ends of outer cage 1500.

In some embodiments, for example during delivery into the vessel, contraction of outer cage 1500 applies radially inward force on inner cage 1506, causing it to contract as well.

In some embodiments, a single control mechanism, such as a push-pull cable coupled to outer cage 1500 simultaneously controls both cages, for example by having outer cage 1500 apply force on inner cage 1506 during contraction. Alternatively, the cages are controlled by separate mechanisms. Optionally, the separate mechanisms involve an inner delivery system configured within an outer delivery system. Optionally, separate control over the cages provides for controlling flow (e.g. axial and/or radial blood flow) through the cages. In an example, the inner cage is contracted and/or the outer cage is expanded to produce a radial gap between the cages, distancing the over-layered openings away from each other and reducing the density so that at least partial flow is allowed through. Optionally, the position of the expandable member in the vessel is maintained by having outer cage 1500 lean against the vessel walls, while control of flow is provided by manipulation of inner cage 1506, such as by approximating the walls of the cages to obstruct flow to the aneurysm, contracting and/or axially sliding one or both of the cages to change the extent of overlap between them, and/or other manipulations.

In FIG. 15B, inner cage 1506 is coupled to outer cage 1500 via a plurality of attachment points 1510. In some embodiments, attachment points 1510 are located at non-junction sections of the wires that form the expandable member. Optionally, an attachment point 1510 is located at a distance from a junction 1512, for example located at ½, ⅓, ¼ or intermediate, larger or smaller fractions of the length of a wire segment extending between neighboring junctions 1512 and 1514.

In some embodiments, attachment point 1510 comprises a welded connection between wires of both cages. Additionally or alternatively, the wires are glued to each other at attachment point 1510.

In some embodiments, the number and/or distribution of attachment points are selected to maintain the cages coupled together. Optionally, the number and/or distribution of attachment points are selected to allow at least some movement of the cages relative to each other, such as axial movement.

A potential advantage of locating the attachment points along non-junction segments of the wires may include reducing a restricting effect of the coupling between the cages during expansion and/or contraction of the member. Optionally, the coupling at non-junction segments reduces a risk of mechanical deformation of the expandable member.

Additionally or alternatively, one or more attachment points are located at junctions between the wires of the cages.

FIGS. 16A-16B and FIGS. 17A-17D describe exemplary wire arrangements of an expandable member in which one or more portions comprise a higher density of openings than one or more other portions of the expandable member, according to some embodiments of the invention. In some embodiments, a longitudinal segment of the expandable member which is intended to be aligned with the aneurysm neck comprises openings of smaller surface area than other segments of the expandable member, such as the proximal and/or distal segments. By positioning a more dense portion of the member at the aneurysm neck, radial flow into and/or from the aneurysm can be reduced, while flow such as axial flow through the vessel passes more freely through the larger openings of the less dense portions of the member, such as in proximity to the distal and/or proximal ends of the member.

It is noted that in some embodiments, the more dense portion may comprise only a peripheral wall portion of the expandable member, which may be angularly oriented to be positioned in front of the aneurysm neck (for example as opposed to a longitudinal section which encompasses a full circumference of the member).

FIGS. 16A-16B show a section 1600 of an expandable member in which the density of openings is changed by pairing wires together (16A), and an enlarged view of a portion of the section (16B), according to some embodiments of the invention.

In an example, two wires 1602 and 1604 comprised within the wire arrangement that forms the more dense portion 1608 of the member are paired to form a double stranded wire 1606 that extends into a less dense portion 1610 of the member. Optionally, the wires are paired in proximity to a distal and/or proximal end of the expandable member. Optionally, the wires are paired by interweaving them together, by welding them together (e.g. by thermal treatment), and/or by other coupling methods.

In some embodiments, as shown for example in the enlarged view of FIG. 16B, pairing of the wires produces openings of a larger surface area as compared to the openings defined between the separated wires. In an example, a ratio between a large opening 1612 defined by the paired wires and a smaller opening 1614 defined by the separate wires is between 1.5:1 to 1.9:1. In another example, if the wires are paired by a gradual wire pairing (e.g. two wires paired into one double stranded wire, and then two double stranded wires are paired into one 4-stranded wire), a ratio between an opening at a more dense portion of the member and an opening at a less dense portion of the member may range between, for example, 1:3, 1:3.5, 1:3.8 or intermediate, larger or smaller ratios.

In an exemplary configuration, a 42 wire structure at more dense portion 1608 is reduced to a 21 double-strand wire structure at less dense portion 1610. In another exemplary configuration, a 16 wire structure at more dense portion 1608 is reduced to an 8 wire structure at less dense portion 1610.

In some embodiments, the expandable member comprises a stepwise reduction of the effective number of wires forming each section, for example by having two wires paired into a double stranded wire, and then two double stranded wires paired into a quadratic stranded wire. In such configuration, an exemplary expandable member comprising 16 wires at a more dense portion can be reduced to an effective 4 wire structure at the least dense portion.

In some embodiments, an odd number of wires (e.g. 3 wires, 5 wires, 3 double stranded wires, etc) may be coupled to each other at a single coupling point.

FIGS. 17A-17D illustrate a wire arrangement in which a plurality of wires comprised within a more dense portion 1700 of the expandable member 1706 (shown in FIG. 17A, and in an enlarged view in FIG. 17B) terminate at the transformation to less dense portion(s) 1702, reducing the number of wires at the less dense portion and thereby increasing the size of the openings defined at the less dense portion, according to some embodiments. The more dense portion 1700 is shown at a cross section in FIG. 17C, the less dense portion 1702 is shown at a cross section in FIG. 17D.

In some embodiments, the wires terminate at a distance 1704 from the proximal and/or distal ends, for example a distance ranging between 3-15 mm, 5-8 mm, 2-10 mm, or intermediate, longer or shorter distances.

In some embodiments, a wire is cut off at its ending point. Additionally or alternatively, a wire ends with a loop, optionally being looped around a second wire that continues to extend to form the less dense portion. A potential advantage of a looped-end wire may include reducing a risk of the free ends interfering with axial movement of the expandable member, for example within the outer tube. Another potential advantage may include reducing a risk of the free ends pricking the vessel wall and/or anchoring against the wall.

In some embodiments, the terminating wires are interweaved with the continuing wires in a manner that moves the terminating wires along with the continuing wires, for example during expansion and/or contraction of the member.

In an exemplary configuration, a central dense portion 1700 comprises 42 wires, and less dense portion(s) 1702 comprise only 16 wires.

Figure 18:
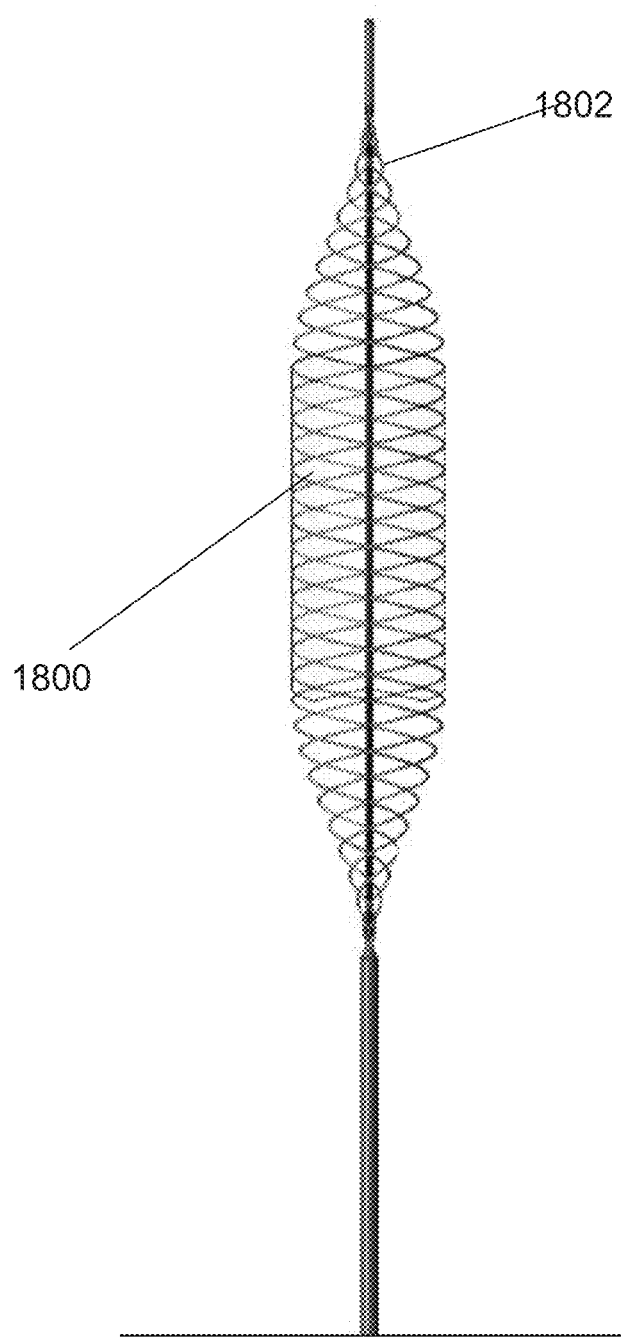
FIG. 18 shows an expandable member comprising a cover, according to some embodiments of the invention.

FIG. 18 illustrates an expandable member comprising a tubular cover 1800 extending over a segment of the member, such as a central segment intended to be positioned in front of the aneurysm neck, according to some embodiments of the invention.

In some embodiments, cover 1800 circumferentially seals the expandable member, reducing (or, in some embodiments, completely eliminating) radial flow to and/or from the aneurysm.

In some embodiments, cover 1800 is formed of an elastic material which can be expanded and/or contracted with the expandable member. Cover 1800 may be formed of silicon, polyurethane, elastic materials and/or dense woven materials. Optionally, a thickness of cover 1800 ranges between, for example, 10-40 micrometer, such as 15 micrometer, 25 micrometer, 35 micrometer or intermediate, larger or smaller thicknesses.

Optionally, cover 1800 does not extend to proximal and/or distal portions of the member, for example ending at a distance of 1-10 mm, 5-10 mm, 6-9 mm or intermediate, longer or shorter distances from an end 1802 (for example the distal end) of the expandable member. Optionally, the axial extent of cover 1800 is selected according to a diameter range of the expandable member.

Figure 19A:
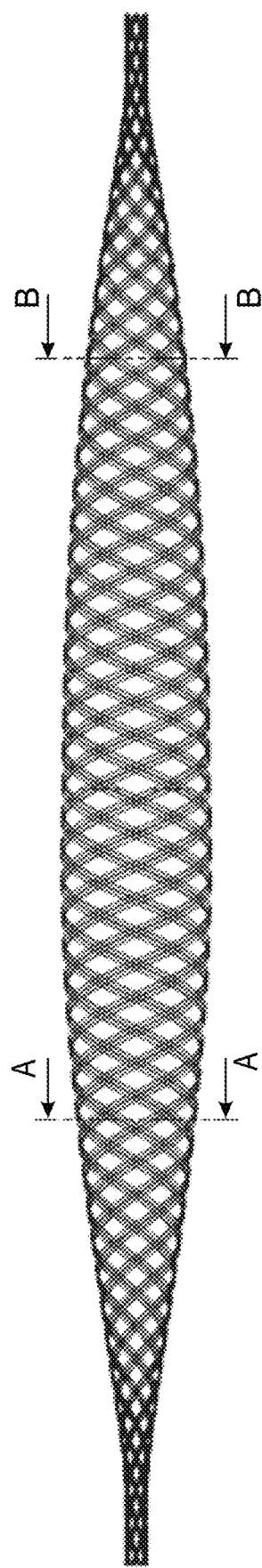
FIGS. 19A-19C show an expandable member comprising wires with a flat cross sectional profile, according to some embodiments of the invention.
Figure 19C:
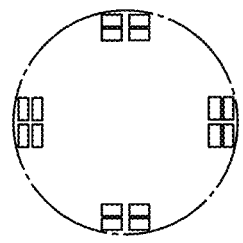
Figure 19B:
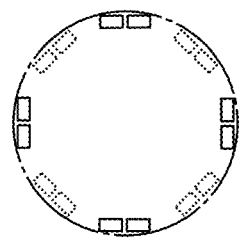

FIGS. 19A-19C illustrate an expandable member comprising wires having a flat cross section profile, according to some embodiments of the invention. In this exemplary configuration, the member comprises a wire pairing for example as described hereinabove. FIG. 19B shows a cross sectional profile of the member along section AA', and FIG. 19C shows a cross sectional profile of the member along section BB', in which the wires are paired.

Some embodiments may comprise wires of different profile, such as circular, elliptical, triangular, and/or other profiles or combinations thereof.

In some embodiments, devices and/or systems and/or methods and/or components as described in one or both of the following applications are incorporated herein by reference:

PCT publication number WO2013/109756A2 filed on Jan. 17, 2013, entitled "METHOD AND APPARATUS FOR OCCLUSION REMOVAL"; and US publication number US2010/0318178 filed on Jun. 15, 2010, entitled "METHOD AND APPARATUS FOR ALLOWING BLOOD FLOW THROUGH AN OCCLUDED VESSEL".

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a cerebral aneurysm, comprising:
   a. positioning an expandable member in a cerebral blood vessel at a location of a cerebral aneurysm, said expandable member comprising:
      i. a braided mesh structure comprising a first distal end and a first proximal end; said braided mesh structure further comprises a plurality of wires arranged to define at least one first wall portion in which openings defined between said wires are small enough to interfere with inner content within said cerebral aneurysm from exiting said cerebral aneurysm;
      ii. a push/pull wire comprising a second distal end and a second proximal end; said second distal end of said push/pull wire being connected to said first distal end of said braided mesh structure; said push/pull wire configured to expand said expandable member from a collapsed configuration to an expanded configuration when said second proximal end of said push/pull wire is actuated;
   b. actuating said second proximal end of said push/pull wire thereby expanding said expandable member to engage the blood vessel walls;
   c. further actuating said second proximal end of said push/pull wire thereby further expanding said expandable member for causing at least part of said expandable member to slightly protrude into a neck of said cerebral aneurysm;
   d. allowing said first wall portion to interfere with inner content of said cerebral aneurysm exiting said cerebral aneurysm; and
   e. actuating said second proximal end of said push/pull wire thereby contracting said expandable member;
   f. removing said expandable member.

2. The method according to claim 1, wherein said expandable member further comprises at least one second wall portion in which openings defined between said wires are large enough to allow blood flow through; said second wall portion axially aligned relative to said first wall portion.

3. The method according to claim 2, further comprising allowing said blood flow to flow through said second wall portion.

4. The method according to claim 1, wherein said inner content comprises blood contained within said cerebral aneurysm.

5. The method according to claim 1, wherein said inner content comprises intra-aneurismal coils that were previously introduced into said aneurysm.

6. The method according to claim 1, comprising reducing radial flow into and/or out said aneurysm enough to allow a thrombus to form.

7. The method according to claim 1, further comprising adjusting a diameter of said expandable member from outside the patient's body; and
   retracting a delivery system used for said positioning to temporarily or permanently deploy said expandable member in said vessel.

8. The method according to claim 7, wherein said adjusting is performed based on a clotting rate of blood at a location of said aneurysm.

9. The method according to claim 8, wherein said method further comprises delivering one or more coils into said aneurysm to induce clotting.

10. The method according to claim 9, wherein said one or more coils are delivered into said aneurysm through a lumen of said expandable member.

11. The method according to claim 9, wherein said one or more coils are delivered into said aneurysm via a microcatheter at least partially axially aligned with said expandable member, and wherein said method further comprises expanding a diameter of said expandable member to capture said microcatheter between said expandable member and a wall of said blood vessel to prevent movement of said microcatheter during coil delivery and removing said microcatheter after coils are delivered and further expanding a diameter of said expandable member.

* * * * *